United States Patent
Gurney et al.

(10) Patent No.: US 8,158,757 B2
(45) Date of Patent: *Apr. 17, 2012

(54) COMPOSITIONS AND METHODS FOR TREATING AND DIAGNOSING CANCER

(75) Inventors: Austin L. Gurney, San Francisco, CA (US); Aaron K. Sato, Burlingame, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/167,172

(22) Filed: Jul. 2, 2008

(65) Prior Publication Data
US 2009/0191205 A1     Jul. 30, 2009

Related U.S. Application Data

(60) Provisional application No. 60/947,611, filed on Jul. 2, 2007.

(51) Int. Cl.
    *C12P 21/08* (2006.01)
(52) U.S. Cl. .................. 530/387.3; 435/328; 435/331
(58) Field of Classification Search .................. None
    See application file for complete search history.

(56) References Cited

U.S. PATENT DOCUMENTS

| | | | |
|---|---|---|---|
| 6,004,528 | A | 12/1999 | Bergstein |
| 7,498,416 | B2 * | 3/2009 | Yayon et al. ............ 530/387.1 |
| 7,541,431 | B2 | 6/2009 | Yoon |
| 2005/0232927 | A1 | 10/2005 | Clarke et al. |
| 2006/0019256 | A1 | 1/2006 | Clarke et al. |
| 2007/0117751 | A1 | 5/2007 | Gurney et al. |
| 2007/0244061 | A1 | 10/2007 | Niehrs et al. |
| 2008/0064049 | A1 | 3/2008 | Clarke et al. |
| 2008/0131434 | A1 | 6/2008 | Lewicki et al. |
| 2009/0208484 | A1 | 8/2009 | Christiano |
| 2010/0071078 | A1 | 3/2010 | Niehrs |

FOREIGN PATENT DOCUMENTS

| | | |
|---|---|---|
| DE | 10339820 A1 | 3/2005 |
| EP | 2 157 192 A1 | 2/2010 |
| EP | 1 673 475 B1 | 4/2010 |
| WO | 99/15660 * | 1/1999 |
| WO | 01/87338 * | 11/2001 |
| WO | WO 02/12447 A2 | 2/2002 |
| WO | 02/102972 * | 12/2002 |
| WO | WO 03/050502 A2 | 6/2003 |
| WO | WO 2004/074436 | 9/2004 |
| WO | WO 2005/040418 | 5/2005 |
| WO | WO 2006/110581 A2 | 10/2006 |
| WO | 2007/096149 * | 8/2007 |
| WO | WO 2008/042236 A2 | 4/2008 |
| WO | WO 2008/046649 A1 | 4/2008 |
| WO | WO 2008/088524 A2 | 7/2008 |
| WO | WO 2010/121923 A1 | 10/2010 |
| WO | WO 2011/076932 A1 | 6/2011 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Campbell Monoclonal Antibody Technology, Elseivers Science Publishers pp. 1-32 (1984).*
Hajj-Al, M., et al., "Prospective identification of tumorigenic breast cancer cells," *Proc. Natl. Acad. Sci. USA* 100:3983-3988, National Academy of Sciences (2003).
Nam, J.-S., et al., "Mouse Cristin/R-spondin Family Proteins are Novel Ligands of the Frizzled 8 and LRP6 Receptors and Activate β-Catenin-dependent Gene Expression," *J. Biol. Chem.* 281:13247-13257, American Society for Biochemistry and Molecular Biology (May 2006).
Hsu, S.Y., et al., "Activation of Orphan Receptors by the Hormone Relaxin," *Science*, 295:671-674, American Association for the Advancement of Science, United States (Jan. 25, 2002).
International Search Report for International Application No. PCT/US2008/008210, European Patent Office, Netherlands, mailed on Mar. 2, 2009.
Mazerbourg, S., et al., "Leucine-Rich Repeat-Containing, G Protein-Coupled Receptor 4 Null Mice Exhibit Intrauterine Growth Retardation Associated with Embryonic and Perinatal Lethality," *Molecular Endocrinology*, 18(9):2241-2254, The Endocrine Society, United States (2004).
McClanahan, T., et al., "Identification of Overexpression of Orphan G Protein-Coupled Receptor GPR49 in Human Colon and Ovarian Primary Tumors," *Cancer Biology and Therapy*, 5(4):419-426, Landes Bioscience, United States (Apr. 2006).

(Continued)

*Primary Examiner* — Sheela J Huff
(74) *Attorney, Agent, or Firm* — Sterne, Kessler, Goldstein & Fox P.L.L.C.

(57) ABSTRACT

The present invention relates to compositions and methods for characterizing, diagnosing and treating cancer. In particular, the present invention identifies LGR5 as a protein overexpressed in solid tumor stem cell. The present invention further identifies an interaction between RSPO1 and LGR5 as an alternative pathway for the activation of beta-catenin signaling. In certain embodiments, the present invention provides biomolecules that disrupt functional signaling via a LGR protein, including, in certain embodiments, molecules that inhibit the interaction between one or more RSPO proteins and one or more LGR proteins, such as LGR5. In certain embodiments, the present invention provides methods of treating cancer comprising disrupting functional LGR signaling and inhibiting growth of a solid tumor comprising solid tumor stem cells.

17 Claims, 12 Drawing Sheets

OTHER PUBLICATIONS

Morita, H., et al., "Neonatal Lethality of LGR5 Null Mice is Associated with Ankyloglossia and Gastrointestinal Distension," *Mol. Cell. Biol.*, 24(22):9736-9743, American Society for Microbiology, United States (Nov. 2004).

Zhao, J., et al., "R-spondin1, A Novel Intestinotrophic Mitogen, Ameliorates Experimental Colitis in Mice," *Gastroenterology*, 132(4)1331-1334, Elsevier, United States (Apr. 2007).

The Written Opinion of the International Searching Authority for International Application No. PCT/US2008/008210, European Patent Office, Netherlands, mailed on Jan. 5, 2010.

* cited by examiner

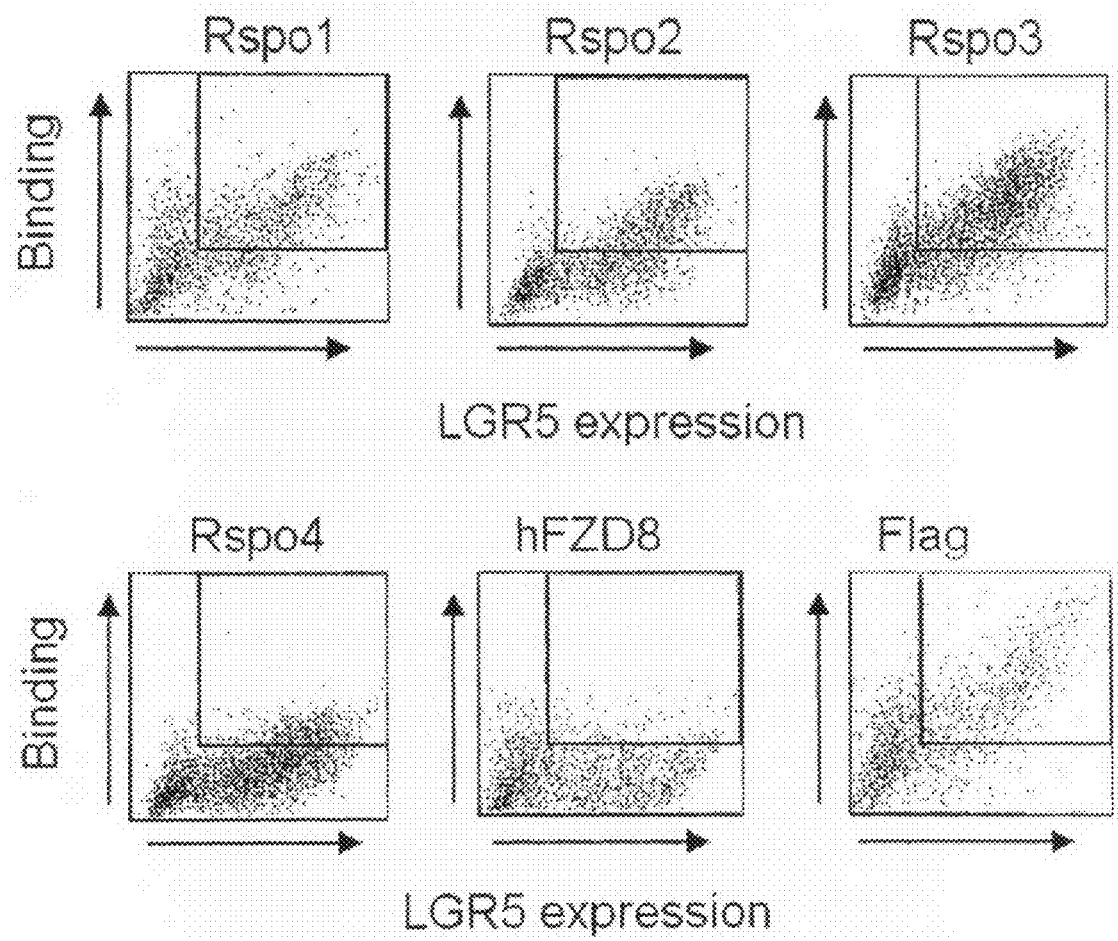

SEQUENCE LISTING

<160> NUMBER OF SEQ ID NOS: 47

<210> SEQ ID NO 1
<211> LENGTH: 543
<212> TYPE: PRT
<213> ORGANISM: Artificial Sequence
<220> FEATURE:
<223> OTHER INFORMATION: Synthetic LGR5 ECD Antibody

<400> SEQUENCE: 1

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Leu Pro Asn Pro
    50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
            100                 105                 110

Leu Gln Asn Leu Arg Ser Leu Gln Ser Leu Arg Leu Asp Ala Asn His
        115                 120                 125

Ile Ser Tyr Val Pro Pro Ser Cys Phe Ser Gly Leu His Ser Leu Arg
    130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
            180                 185                 190

Val Leu His Leu His Asn Asn Arg Ile His Ser Leu Gly Lys Lys Cys
        195                 200                 205

Phe Asp Gly Leu His Ser Leu Glu Thr Leu Asp Leu Asn Tyr Asn Asn
    210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
                245                 250                 255

```
Val Gly Asn Pro Ser Leu Ile Thr Ile His Phe Tyr Asp Asn Pro Ile
            260                 265                 270

Gln Phe Val Gly Arg Ser Ala Phe Gln His Leu Pro Glu Leu Arg Thr
        275                 280                 285

Leu Thr Leu Asn Gly Ala Ser Gln Ile Thr Glu Phe Pro Asp Leu Thr
290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
        355                 360                 365

Lys Val Asp Thr Phe Gln Gln Leu Leu Ser Leu Arg Ser Leu Asn Leu
370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Ile Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
        435                 440                 445

Val Ile Glu Met Pro Tyr Ala Tyr Gln Cys Cys Ala Phe Gly Val Cys
450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
        515                 520                 525

Pro Cys Glu His Leu Leu Asp Gly Trp Leu Ile Arg Ile Gly Val
530                 535                 540

<210> SEQ ID NO 2
<211> LENGTH: 792
<212> TYPE: DNA
<213> ORGANISM: Homo sapiens

<400> SEQUENCE: 2
atgcggcttg ggctgtgtgt ggtggccctg gttctgagct ggacgcacct caccatcagc     60
agccggggga tcaagggggaa aaggcagagg cggatcagtg ccgaggggag ccaggcctgt    120
gccaaaggct gtgagctctg ctctgaagtc aacggctgcc tcaagtgctc acccaagctg    180
ttcatcctgc tggagaggaa cgacatccgc caggtgggcg tctgcttgcc gtcctgccca    240
cctggatact cgacgcccg caaccccgac atgaacaagt gcatcaaatg caagatcgag    300
cactgtgagg cctgcttcag ccataacttc tgcaccaagt gtaaggaggg cttgtacctg    360
cacaagggcc gctgctatcc agcttgtccc gagggctcct cagctgccaa tggcaccatg    420
gagtgcagta gtcctgcgca atgtgaaatg agcgagtggt ctccgtgggg gccctgctcc    480
aagaagcagc agctctgtgg tttccggagg ggctccgagg agcggacacg cagggtgcta    540
```

-continued

```
catgcccctg tgggggacca tgctgcctgc tctgacacca aggagacccg gaggtgcaca      600
gtgaggagag tgccgtgtcc tgagggcag  aagaggagga agggaggcca gggccggcgg      660
gagaatgcca acaggaacct ggccaggaag gagagcaagg aggcgggtgc tggctctcga      720
agacgcaagg ggcagcaaca gcagcagcag caagggacag tggggccact cacatctgca      780
gggcctgcct ag                                                          792
```

<210> SEQ ID NO 3
<211> LENGTH: 263
<212> TYPE: PRT
<213> ORGANISM: Homo sapiens

<400> SEQUENCE: 3

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260
```

<210> SEQ ID NO 4
<211> LENGTH: 732
<212> TYPE: DNA
<213> ORGANISM: Homo sapiens

<400> SEQUENCE: 4

```
atgcagtttc gccttttctc ctttgcctc  atcattctga actgcatgga ttacagccac      60
tgccaaggca accgatggag acgcagtaag cgagctagtt atgtatcaaa tcccatttgc     120
```

-continued

```
aagggttgtt tgtcttgttc aaaggacaat gggtgtagcc gatgtcaaca gaagttgttc      180
ttcttccttc gaagagaagg gatgcgccag tatggagagt gcctgcattc ctgcccatcc      240
gggtactatg gacaccgagc cccagatatg aacagatgtg caagatgcag aatagaaaac      300
tgtgattctt gctttagcaa agactttgt accaagtgca agtaggctt ttatttgcat        360 agaggccgtt gctttgatga atgtccagat ggttttgcac cattagaaga accatggaa       420 tgtgtggaag gatgtgaagt tggtcattgg agcgaatggg gaacttgtag cagaaataat      480
cgcacatgtg gatttaaatg gggtctggaa accagaacac ggcaaattgt taaaaagcca      540
gtgaaagaca caataccgtg tccaaccatt gctgaatcca ggagatgcaa gatgacaatg      600
aggcattgtc caggagggaa gagaacacca aaggcgaagg agaagaggaa caagaaaaag      660
aaaaggaagc tgatagaaag ggcccaggag caacacagcg tcttcctagc tacagacaga      720
gctaaccaat aa                                                          732
```

<210> SEQ ID NO 5
<211> LENGTH: 243
<212> TYPE: PRT
<213> ORGANISM: Homo sapiens

<400> SEQUENCE: 5

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Pro Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln
```

<210> SEQ ID NO 6

```
<211> LENGTH: 819
<212> TYPE: DNA
<213> ORGANISM: Homo sapiens

<400> SEQUENCE: 6
atgcacttgc gactgatttc ttggcttttt atcattttga actttatgga atacatcggc      60
agccaaaacg cctcccgggg aaggcgccag cgaagaatgc atcctaacgt tagtcaaggc     120
tgccaaggag ctgtgcaac atgctcagat tacaatggga gtttgtcatg taagcccaga     180
ctattttttg ctctggaaag aattggcatg aagcagattg gagtatgtct ctcttcatgt     240
ccaagtggat attatggaac tcgatatcca gatataaata gtgtacaaa atgcaaagct     300 gactgtgata cctgtttcaa caaaaatttc tgcacaaaat gtaaaagtgg attttactta     360
caccttggaa agtgccttga caattgccca gaagggttgg aagccaacaa ccatactatg     420
gagtgtgtca gtattgtgca ctgtgaggtc agtgaatgga tccttggag tccatgcacg     480 aagaagggaa aaacatgtgg cttcaaaaga gggactgaaa cacgggtccg agaaataata     540
cagcatcctt cagcaaaggg taacctgtgt cccccaacaa atgagacaag aaagtgtaca     600
gtgcaaagga gaagtgtca gaagggagaa cgaggaaaaa aaggaaggga gaggaaaaga     660
aaaaaaccta ataaggaga agtaaagaa gcaatacctg acagcaaaag tctggaatcc     720
agcaaagaaa tcccagagca acgagaaaac aaacagcagc agaagaagcg aaaagtccaa     780
gataaacaga aatcggtatc agtcagcact gtacactag                           819

<210> SEQ ID NO 7
<211> LENGTH: 272
<212> TYPE: PRT
<213> ORGANISM: Homo sapiens

<400> SEQUENCE: 7

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Cys Gln Lys
        195                 200                 205
```

Gly Glu Arg Gly Lys Lys Gly Arg Glu Arg Lys Arg Lys Pro Asn
            210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270

<210> SEQ ID NO 8
<211> LENGTH: 705
<212> TYPE: DNA
<213> ORGANISM: Homo sapiens

<400> SEQUENCE: 8

```
atgcgggcgc cactctgcct gctcctgctc gtcgcccacg ccgtggacat gctcgccctg      60
aaccgaagga agaagcaagt gggcactggc ctggggggca actgcacagg ctgtatcatc     120
tgctcagagg agaacggctg ttccacctgc agcagaggc tcttcctgtt catccgccgg      180
gaaggcatcc gccagtacgg caagtgcctg cacgactgtc ccctgggta cttcggcatc      240
cgcggccagg aggtcaacag gtgcaaaaaa tgtggggcca cttgtgagag ctgcttcagc     300
caggacttct gcatccggtg caagaggcag ttttacttgt acaaggggaa gtgtctgccc     360
acctgcccgc cgggcacttt ggcccaccag aacacacggg agtgccaggg ggagtgtgaa     420
ctgggtccct ggggcggctg gagccccctgc acacacaatg aaagacctg cggctcgcct     480
tggggcctgg agagccgggt acgagaggct ggccgggctg gcatgagga ggcagccacc     540
tgccaggtgc tttctgagtc aaggaaatgt cccatccaga ggccctgccc aggagagagg     600
agccccggcc agaagaaggg caggaaggac cggcgcccac gcaaggacag gaagctggac     660
cgcaggctgg acgtgaggcc gcgccagccc ggcctgcagc cctga                    705
```

<210> SEQ ID NO 9
<211> LENGTH: 234
<212> TYPE: PRT
<213> ORGANISM: Homo sapiens

<400> SEQUENCE: 9

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

```
Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
210                 215                 220

Val Arg Pro Arg Gln Pro Gly Leu Gln Pro
225                 230

<210> SEQ ID NO 10
<211> LENGTH: 951
<212> TYPE: PRT
<213> ORGANISM: Homo sapiens

<400> SEQUENCE: 10

Met Pro Gly Pro Leu Gly Leu Leu Cys Phe Leu Ala Leu Gly Leu Leu
1               5                   10                  15

Gly Ser Ala Gly Pro Ser Gly Ala Ala Pro Pro Leu Cys Ala Ala Pro
            20                  25                  30

Cys Ser Cys Asp Gly Asp Arg Arg Val Asp Cys Ser Gly Lys Gly Leu
        35                  40                  45

Thr Ala Val Pro Glu Gly Leu Ser Ala Phe Thr Gln Ala Leu Asp Ile
    50                  55                  60

Ser Met Asn Asn Ile Thr Gln Leu Pro Glu Asp Ala Phe Lys Asn Phe
65                  70                  75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Arg Ser Leu Ser Gln His Cys Phe Asp Gly Leu
210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Phe Val Gly
        275                 280                 285
```

-continued

```
Asn Ser Ala Phe His Asn Leu Ser Asp Leu His Ser Leu Val Ile Arg
    290                 295                 300
Gly Ala Ser Met Val Gln Gln Phe Pro Asn Leu Thr Gly Thr Val His
305                 310                 315                 320
Leu Glu Ser Leu Thr Leu Thr Gly Thr Lys Ile Ser Ser Ile Pro Asn
                325                 330                 335
Asn Leu Cys Gln Glu Gln Lys Met Leu Arg Thr Leu Asp Leu Ser Tyr
                340                 345                 350
Asn Asn Ile Arg Asp Leu Pro Ser Phe Asn Gly Cys His Ala Leu Glu
                355                 360                 365
Glu Ile Ser Leu Gln Arg Asn Gln Ile Tyr Gln Ile Lys Glu Gly Thr
    370                 375                 380
Phe Gln Gly Leu Ile Ser Leu Arg Ile Leu Asp Leu Ser Arg Asn Leu
385                 390                 395                 400
Ile His Glu Ile His Ser Arg Ala Phe Ala Thr Leu Gly Pro Ile Thr
                405                 410                 415
Asn Leu Asp Val Ser Phe Asn Glu Leu Thr Ser Phe Pro Thr Glu Gly
                420                 425                 430
Leu Asn Gly Leu Asn Gln Leu Lys Leu Val Gly Asn Phe Lys Leu Lys
                435                 440                 445
Glu Ala Leu Ala Ala Lys Asp Phe Val Asn Leu Arg Ser Leu Ser Val
    450                 455                 460
Pro Tyr Ala Tyr Gln Cys Cys Ala Phe Trp Gly Cys Asp Ser Tyr Ala
465                 470                 475                 480
Asn Leu Asn Thr Glu Asp Asn Ser Leu Gln Asp His Ser Val Ala Gln
                485                 490                 495
Glu Lys Gly Thr Ala Asp Ala Ala Asn Val Thr Ser Thr Leu Glu Asn
                500                 505                 510
Glu Glu His Ser Gln Ile Ile Ile His Cys Thr Pro Ser Thr Gly Ala
    515                 520                 525
Phe Lys Pro Cys Glu Tyr Leu Leu Gly Ser Trp Met Ile Arg Leu Thr
530                 535                 540
Val Trp Phe Ile Phe Leu Val Ala Leu Phe Phe Asn Leu Leu Val Ile
545                 550                 555                 560
Leu Thr Thr Phe Ala Ser Cys Thr Ser Leu Pro Ser Ser Lys Leu Phe
                565                 570                 575
Ile Gly Leu Ile Ser Val Ser Asn Leu Phe Met Gly Ile Tyr Thr Gly
                580                 585                 590
Ile Leu Thr Phe Leu Asp Ala Val Ser Trp Gly Arg Phe Ala Glu Phe
    595                 600                 605
Gly Ile Trp Trp Glu Thr Gly Ser Gly Cys Lys Val Ala Gly Phe Leu
610                 615                 620
Ala Val Phe Ser Ser Glu Ser Ala Ile Phe Leu Leu Met Leu Ala Thr
625                 630                 635                 640
Val Glu Arg Ser Leu Ser Ala Lys Asp Ile Met Lys Asn Gly Lys Ser
                645                 650                 655
Asn His Leu Lys Gln Phe Arg Val Ala Ala Leu Leu Ala Phe Leu Gly
                660                 665                 670
Ala Thr Val Ala Gly Cys Phe Pro Leu Phe His Arg Gly Glu Tyr Ser
    675                 680                 685
Ala Ser Pro Leu Cys Leu Pro Phe Pro Thr Gly Glu Thr Pro Ser Leu
690                 695                 700
Gly Phe Thr Val Thr Leu Val Leu Leu Asn Ser Leu Ala Phe Leu Leu
705                 710                 715                 720
```

```
Met Ala Val Ile Tyr Thr Lys Leu Tyr Cys Asn Leu Glu Lys Glu Asp
                725                 730                 735

Leu Ser Glu Asn Ser Gln Ser Ser Met Ile Lys His Val Ala Trp Leu
                740                 745                 750

Ile Phe Thr Asn Cys Ile Phe Cys Pro Val Ala Phe Phe Ser Phe
                755                 760                 765

Ala Pro Leu Ile Thr Ala Ile Ser Ile Ser Pro Glu Ile Met Lys Ser
                770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
                805                 810                 815

Arg Arg Val Thr Lys Lys Ser Gly Ser Val Ser Val Ser Ile Ser Ser
                820                 825                 830

Gln Gly Gly Cys Leu Glu Gln Asp Phe Tyr Tyr Asp Cys Gly Met Tyr
                835                 840                 845

Ser His Leu Gln Gly Asn Leu Thr Val Cys Asp Cys Cys Glu Ser Phe
                850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
                885                 890                 895

Ser Asp Cys Gly Thr Gln Ser Ala His Ser Asp Tyr Ala Asp Glu Glu
                900                 905                 910

Asp Ser Phe Val Ser Asp Ser Ser Asp Gln Val Gln Ala Cys Gly Arg
                915                 920                 925

Ala Cys Phe Tyr Gln Ser Arg Gly Phe Pro Leu Val Arg Tyr Ala Tyr
                930                 935                 940

Asn Leu Pro Arg Val Lys Asp
945                 950

<210> SEQ ID NO 11
<211> LENGTH: 915
<212> TYPE: PRT
<213> ORGANISM: Homo sapiens

<400> SEQUENCE: 11

Met Gly Arg Pro Arg Leu Thr Leu Val Cys Gln Val Ser Ile Ile Ile
1               5                   10                  15

Ser Ala Arg Asp Leu Ser Met Asn Asn Leu Thr Glu Leu Gln Pro Gly
                20                  25                  30

Leu Phe His His Leu Arg Phe Leu Glu Glu Leu Arg Leu Ser Gly Asn
                35                  40                  45

His Leu Ser His Ile Pro Gly Gln Ala Phe Ser Gly Leu Tyr Ser Leu
                50                  55                  60

Lys Ile Leu Met Leu Gln Asn Asn Gln Leu Gly Gly Ile Pro Ala Glu
65                  70                  75                  80

Ala Leu Trp Glu Leu Pro Ser Leu Gln Ser Leu Arg Leu Asp Ala Asn
                85                  90                  95

Leu Ile Ser Leu Val Pro Glu Arg Ser Phe Glu Gly Leu Ser Ser Leu
                100                 105                 110

Arg His Leu Trp Leu Asp Asp Asn Ala Leu Thr Glu Ile Pro Val Arg
                115                 120                 125

Ala Leu Asn Asn Leu Pro Ala Leu Gln Ala Met Thr Leu Ala Leu Asn
                130                 135                 140
```

```
Arg Ile Ser His Ile Pro Asp Tyr Ala Phe Gln Asn Leu Thr Ser Leu
145                 150                 155                 160

Val Val Leu His Leu His Asn Asn Arg Ile Gln His Leu Gly Thr His
                165                 170                 175

Ser Phe Glu Gly Leu His Asn Leu Glu Thr Leu Asp Leu Asn Tyr Asn
            180                 185                 190

Lys Leu Gln Glu Phe Pro Val Ala Ile Arg Thr Leu Gly Arg Leu Gln
        195                 200                 205

Glu Leu Gly Phe His Asn Asn Asn Ile Lys Ala Ile Pro Glu Lys Ala
    210                 215                 220

Phe Met Gly Asn Pro Leu Leu Gln Thr Ile His Phe Tyr Asp Asn Pro
225                 230                 235                 240

Ile Gln Phe Val Gly Arg Ser Ala Phe Gln Tyr Leu Pro Lys Leu His
                245                 250                 255

Thr Leu Ser Leu Asn Gly Ala Met Asp Ile Gln Glu Phe Pro Asp Leu
            260                 265                 270

Lys Gly Thr Thr Ser Leu Glu Ile Leu Thr Leu Thr Arg Ala Gly Ile
        275                 280                 285

Arg Leu Leu Pro Ser Gly Met Cys Gln Gln Leu Pro Arg Leu Arg Val
    290                 295                 300

Leu Glu Leu Ser His Asn Gln Ile Glu Glu Leu Pro Ser Leu His Arg
305                 310                 315                 320

Cys Gln Lys Leu Glu Glu Ile Gly Leu Gln His Asn Arg Ile Trp Glu
                325                 330                 335

Ile Gly Ala Asp Thr Phe Ser Gln Leu Ser Ser Leu Gln Ala Leu Asp
            340                 345                 350

Leu Ser Trp Asn Ala Ile Arg Ser Ile His Pro Glu Ala Phe Ser Thr
        355                 360                 365

Leu His Ser Leu Val Lys Leu Asp Leu Thr Asp Asn Gln Leu Thr Thr
    370                 375                 380

Leu Pro Leu Ala Gly Leu Gly Gly Leu Met His Leu Lys Leu Lys Gly
385                 390                 395                 400

Asn Leu Ala Leu Ser Gln Ala Phe Ser Lys Asp Ser Phe Pro Lys Leu
                405                 410                 415

Arg Ile Leu Glu Val Pro Tyr Ala Tyr Gln Cys Cys Pro Tyr Gly Met
            420                 425                 430

Cys Ala Ser Phe Phe Lys Ala Ser Gly Gln Trp Glu Ala Glu Asp Leu
        435                 440                 445

His Leu Asp Asp Glu Glu Ser Ser Lys Arg Pro Leu Gly Leu Leu Ala
    450                 455                 460

Arg Gln Ala Glu Asn His Tyr Asp Gln Asp Leu Asp Glu Leu Gln Leu
465                 470                 475                 480

Glu Met Glu Asp Ser Lys Pro His Pro Ser Val Gln Cys Ser Pro Thr
                485                 490                 495

Pro Gly Pro Phe Lys Pro Cys Glu Tyr Leu Phe Glu Ser Trp Gly Ile
            500                 505                 510

Arg Leu Ala Val Trp Ala Ile Val Leu Leu Ser Val Leu Cys Asn Gly
        515                 520                 525

Leu Val Leu Leu Thr Val Phe Ala Gly Pro Val Pro Leu Pro Pro
    530                 535                 540

Val Lys Phe Val Val Gly Ala Ile Ala Gly Ala Asn Thr Leu Thr Gly
545                 550                 555                 560

Ile Ser Cys Gly Leu Leu Ala Ser Val Asp Ala Leu Thr Phe Gly Gln
```

```
                    565                 570                 575
Phe Ser Glu Tyr Gly Ala Arg Trp Glu Thr Gly Leu Gly Cys Arg Ala
            580                 585                 590

Thr Gly Phe Leu Ala Val Leu Gly Ser Glu Ala Ser Val Leu Leu Leu
        595                 600                 605

Thr Leu Ala Ala Val Gln Cys Ser Val Ser Val Ser Cys Val Arg Ala
    610                 615                 620

Tyr Gly Lys Ser Pro Ser Leu Gly Ser Val Arg Ala Gly Val Leu Gly
625                 630                 635                 640

Cys Leu Ala Leu Ala Gly Leu Ala Ala Ala Leu Pro Leu Ala Ser Val
                645                 650                 655

Gly Glu Tyr Gly Ala Ser Pro Leu Cys Leu Pro Tyr Ala Pro Pro Glu
            660                 665                 670

Gly Gln Pro Ala Ala Leu Gly Phe Thr Val Ala Leu Val Met Met Asn
        675                 680                 685

Ser Phe Cys Phe Leu Val Val Ala Gly Ala Tyr Ile Lys Leu Tyr Cys
    690                 695                 700

Asp Leu Pro Arg Gly Asp Phe Glu Ala Val Trp Asp Cys Ala Met Val
705                 710                 715                 720

Arg His Val Ala Trp Leu Ile Phe Ala Asp Gly Leu Leu Tyr Cys Pro
                725                 730                 735

Val Ala Phe Leu Ser Phe Ala Ser Met Leu Gly Leu Phe Pro Val Thr
            740                 745                 750

Pro Glu Ala Val Lys Ser Val Leu Leu Val Val Leu Pro Leu Pro Ala
        755                 760                 765

Cys Leu Asn Pro Leu Leu Tyr Leu Leu Phe Asn Pro His Phe Arg Asp
    770                 775                 780

Asp Leu Arg Arg Leu Arg Pro Arg Ala Gly Asp Ser Gly Pro Leu Ala
785                 790                 795                 800

Tyr Ala Ala Ala Gly Glu Leu Glu Lys Ser Ser Cys Asp Ser Thr Gln
                805                 810                 815

Ala Leu Val Ala Phe Ser Asp Val Asp Leu Ile Leu Glu Ala Ser Glu
            820                 825                 830

Ala Gly Arg Pro Pro Gly Leu Glu Thr Tyr Gly Phe Pro Ser Val Thr
        835                 840                 845

Leu Ile Ser Cys Gln Gln Pro Gly Ala Pro Arg Leu Glu Gly Ser His
    850                 855                 860

Cys Val Glu Pro Glu Gly Asn His Phe Gly Asn Pro Gln Pro Ser Met
865                 870                 875                 880

Asp Gly Glu Leu Leu Leu Arg Ala Glu Gly Ser Thr Pro Ala Gly Gly
                885                 890                 895

Gly Leu Ser Gly Gly Gly Gly Phe Gln Pro Ser Gly Leu Ala Phe Ala
            900                 905                 910

Ser His Val
        915

<210> SEQ ID NO 12
<211> LENGTH: 2724
<212> TYPE: DNA
<213> ORGANISM: Homo sapiens

<400> SEQUENCE: 12
atggacacct cccggctcgg tgtgctcctg tccttgcctg tgctgctgca gctggcgacc       60
gggggcagct ctcccaggtc tggtgtgttg ctgaggggct gccccacaca ctgtcattgc      120
```

```
gagcccgacg gcaggatgtt gctcagggtg gactgctccg acctggggct ctcggagctg    180
ccttccaacc tcagcgtctt cacctcctac ctagacctca gtatgaacaa catcagtcag    240
ctgctcccga atcccctgcc cagtctccgc ttcctggagg agttacgtct tgcgggaaac    300
gctctgacat acattcccaa gggagcattc actggccttt acagtcttaa agttcttatg    360
ctgcagaata atcagctaag acacgtaccc acagaagctc tgcagaattt gcgaagcctt    420
caatccctgc gtctggatgc taaccacatc agctatgtgc ccccaagctg tttcagtggc    480
ctgcattccc tgaggcacct gtggctggat gacaatgcgt taacagaaat ccccgtccag    540
gcttttagaa gtttatcggc attgcaagcc atgaccttgg ccctgaacaa aatacaccac    600
ataccagact atgcctttgg aaacctctcc agcttggtag ttctacatct ccataacaat    660
agaatccact ccctgggaaa gaaatgcttt gatgggctcc acagcctaga gactttagat    720
ttaaattaca ataaccttga tgaattcccc actgcaatta ggacactctc caaccttaaa    780
gaactaggat ttcatagcaa caatatcagg tcgatacctg agaaagcatt tgtaggcaac    840
ccttctctta ttacaataca tttctatgac aatcccatcc aatttgttgg gagatctgct    900
tttcaacatt tacctgaact aagaacactg actctgaatg gtgcctcaca ataactgaa     960 tttcctgatt taactggaac tgcaaacctg gagagtctga ctttaactgg agcacagatc   1020
tcatctcttc ctcaaaccgt ctgcaatcag ttacctaatc tccaagtgct agatctgtct   1080
tacaacctat tagaagattt acccagtttt tcagtctgcc aaaagcttca gaaaattgac   1140
ctaagacata atgaaatcta cgaaattaaa gttgacactt tccagcagtt gcttagcctc   1200
cgatcgctga atttggcttg gaacaaaatt gctattattc accccaatgc attttccact   1260
ttgccatccc taataaagct ggacctatcg tccaacctcc tgtcgtcttt tcctataact   1320
gggttacatg gtttaactca cttaaaatta acaggaaatc atgccttaca gagcttgata   1380
tcatctgaaa actttccaga actcaaggtt atagaaatgc ttatgcttta ccagtgctgt   1440
gcatttggag tgtgtgagaa tgcctataag atttctaatc aatggaataa aggtgacaac   1500
agcagtatgg acgaccttca taagaaagat gctggaatgt ttcaggctca agatgaacgt   1560
gaccttgaag atttcctgct tgactttgag gaagacctga agcccttca ttcagtgcag    1620 tgttcacctt ccccaggccc cttcaaaccc tgtgaacacc tgcttgatgg ctggctgatc   1680
agaattggag tgtggaccat agcagttctg gcacttactt gtaatgcttt ggtgacttca   1740
acagttttca gatcccctct gtacatttcc cccattaaac tgttaattgg ggtcatcgca   1800
gcagtgaaca tgctcacggg agtctccagt gccgtgctgg ctggtgtgga tgcgttcact   1860
tttggcagct ttgcacgaca tggtgcctgg tgggagaatg gggttggttg ccatgtcatt   1920
ggttttttgt ccattttgc ttcagaatca tctgtttcc tgcttactct ggcagccctg    1980
gagcgtgggt tctctgtgaa atattctgca aatttgaaa cgaaagctcc attttctagc    2040
ctgaaagtaa tcatttgct ctgtgccctg ctggccttga ccatggccgc agttcccctg    2100
ctgggtggca gcaagtatgg cgcctcccct ctctgcctgc ctttgccttt tggggagccc   2160
agcaccatgg gctacatggt cgctctcatc ttgctcaatt cccttgcttt cctcatgatg   2220
accattgcct acaccaagct ctactgcaat ttggacaagg gagacctgga gaatatttgg   2280
gactgctcta tggtaaaaca cattgccctg ttgctcttca ccaactgcat cctaaactgc   2340
cctgtggctt tcttgtcctt ctcctcttta ataaaccta catttatcag tcctgaagta   2400
attaagttta tccttctggt ggtagtccca cttcctgcat gtctcaatcc ccttctctac   2460
atcttgttca atcctcactt taaggaggat ctggtgagcc tgagaaagca aacctacgtc   2520
```

```
tggacaagat caaaacaccc aagcttgatg tcaattaact ctgatgatgt cgaaaaacag    2580
tcctgtgact caactcaagc cttggtaacc tttaccagct ccagcatcac ttatgacctg    2640
cctcccagtt ccgtgccatc accagcttat ccagtgactg agagctgcca tctttcctct    2700
gtggcatttg tcccatgtct ctaa                                           2724

<210> SEQ ID NO 13
<211> LENGTH: 907
<212> TYPE: PRT
<213> ORGANISM: Homo sapiens

<400> SEQUENCE: 13

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
```

```
                     340                 345                 350
Asn Leu Gln Val Leu Asp Leu Ser Tyr Asn Leu Leu Glu Asp Leu Pro
                355                 360                 365
Ser Phe Ser Val Cys Gln Lys Leu Gln Lys Ile Asp Leu Arg His Asn
370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
                420                 425                 430
Leu Leu Ser Ser Phe Pro Ile Thr Gly Leu His Gly Leu Thr His Leu
                435                 440                 445
Lys Leu Thr Gly Asn His Ala Leu Gln Ser Leu Ile Ser Ser Glu Asn
                450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
                500                 505                 510
Met Phe Gln Ala Gln Asp Glu Arg Asp Leu Glu Asp Phe Leu Leu Asp
                515                 520                 525
Phe Glu Glu Asp Leu Lys Ala Leu His Ser Val Gln Cys Ser Pro Ser
530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
                580                 585                 590
Lys Leu Leu Ile Gly Val Ile Ala Ala Val Asn Met Leu Thr Gly Val
                595                 600                 605
Ser Ser Ala Val Leu Ala Gly Val Asp Ala Phe Thr Phe Gly Ser Phe
                610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
                660                 665                 670
Glu Thr Lys Ala Pro Phe Ser Ser Leu Lys Val Ile Ile Leu Leu Cys
                675                 680                 685
Ala Leu Leu Ala Leu Thr Met Ala Ala Val Pro Leu Leu Gly Gly Ser
                690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
                740                 745                 750
Lys Gly Asp Leu Glu Asn Ile Trp Asp Cys Ser Met Val Lys His Ile
                755                 760                 765
```

```
Ala Leu Leu Leu Phe Thr Asn Cys Ile Leu Asn Cys Pro Val Ala Phe
            770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905
```

<210> SEQ ID NO 14
<211> LENGTH: 2385
<212> TYPE: DNA
<213> ORGANISM: Artificial Sequence
<220> FEATURE:
<223> OTHER INFORMATION: Synthetic LGR5-Fc Antibody

<400> SEQUENCE: 14

```
atggcacct cccggctcgg tgtgctcctg tccttgcctg tgctgctgca gctggcgacc      60
ggggcagct ctcccaggtc tggtgtgttg ctgaggggct gccccacaca ctgtcattgc     120
gagcccgacg gcaggatgtt gctcagggtg gactgctccg acctggggct ctcggagctg    180
ccttccaacc tcagcgtctt cacctcctac ctagacctca gtatgaacaa catcagtcag    240
ctgctcccga atccctgcc cagtctccgc ttcctggagg agttacgtct gcgggaaac    300
gctctgacat acattcccaa gggagcattc actggccttt acagtcttaa agttcttatg    360
ctgcagaata atcagctaag cacgtaccc acagaagctc tgcagaattt gcgaagcctt    420
caatccctgc gtctggatgc taaccacatc agctatgtgc ccccaagctg tttcagtggc    480
ctgcattccc tgaggcacct gtggctggat acaatgcgt taacagaaat ccccgtccag    540
gcttttagaa gttatcggc attgcaagcc atgaccttgg ccctgaacaa atacaccac    600
ataccagact atgcctttgg aaacctctcc agcttggtag ttctacatct ccataacaat    660
agaatccact ccctgggaaa gaatgctttt gatgggctcc acagcctaga gactttagat    720
ttaaattaca ataaccttga tgaattcccc actgcaatta ggacactctc caaccttaaa    780
gaactaggat tcatagcaa caatatcagg tcgatacctg agaaagcatt tgtaggcaac    840
ccttctctta ttacaataca tttctatgac aatcccatcc aatttgttgg gagatctgct    900
tttcaacatt taccctgaact aagaacactg actctgaatg gtgcctcaca aataactgaa    960
tttcctgatt taactggaac tgcaaacctg gagagtctga ctttaactgg agcacagatc   1020
tcatctcttc ctcaaaccgt ctgcaatcag ttacctaatc tccaagtgct agatctgtct   1080
tacaacctat tagaagattt acccagtttt tcagtctgcc aaaagcttca gaaaattgac   1140
ctaagacata atgaaatcta cgaaattaaa gttgacactt ccagcagtt gcttagcctc   1200
cgatcgctga atttggcttg gaacaaaatt gctattattc ccccaatgc atttccact   1260
ttgccatccc taataaagct ggacctatcg tccaacctcc tgtcgtcttt tcctataact   1320
```

```
gggttacatg gtttaactca cttaaaatta acaggaaatc atgccttaca gagcttgata    1380
tcatctgaaa actttccaga actcaaggtt atagaaatgc cttatgctta ccagtgctgt    1440
gcatttggag tgtgtgagaa tgcctataag atttctaatc aatggaataa aggtgacaac    1500
agcagtatgg acgaccttca taagaaagat gctggaatgt tcaggctca agatgaacgt     1560 gaccttgaag atttcctgct tgactttgag gaagacctga agcccttca ttcagtgcag     1620 tgttcacctt ccccaggccc cttcaaaccc tgtgaacacc tgcttgatgg ctggctgatc    1680
agaattggag tggggcgcgc cgacaaaact cacacatgcc caccgtgccc agcacctgaa    1740
ctcctggggg gaccgtcagt cttcctcttc cccccaaaac ccaaggacac cctcatgatc    1800
tcccggaccc ctgaggtcac atgcgtggtg gtggacgtga gccacgaaga ccctgaggtc    1860
aagttcaact ggtacgtgga cggcgtggag gtgcataatg ccaagacaaa gccgcgggag    1920
gagcagtaca acagcacgta ccgtgtggtc agcgtcctca ccgtcctgca ccaggactgg    1980
ctgaatggca aggagtacaa gtgcaaggtc tccaacaaag ccctcccagc ccccatcgag    2040
aaaaccatct ccaaagccaa agggcagccc cgagaaccac aggtgtacac cctgccccca    2100
tcccgggatg agctgaccaa gaaccaggtc agcctgacct gcctggtcaa aggcttctat    2160
cccagcgaca tcgccgtgga gtgggagagc aatgggcagc cggagaacaa ctacaagacc    2220
acgcctcccg tgctggactc cgacggctcc ttcttcctct acagcaagct caccgtggac    2280
aagagcaggt ggcagcaggg gaacgtcttc tcatgctccg tgatgcatga ggctctgcac    2340
aaccactaca cacagaagag cctctcccct gtctccgggta aatga                   2385
```

<210> SEQ ID NO 15  
<211> LENGTH: 794  
<212> TYPE: PRT  
<213> ORGANISM: Artificial Sequence  
<220> FEATURE:  
<223> OTHER INFORMATION: Synthetic LGR5-Fc Antibody

<400> SEQUENCE: 15

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175
```

```
Ile Pro Val Gln Ala Phe Arg Ser Leu Ser Ala Leu Gln Ala Met Thr
            180                 185                 190
Leu Ala Leu Asn Lys Ile His His Ile Pro Asp Tyr Ala Phe Gly Asn
        195                 200                 205
Leu Ser Ser Leu Val Val Leu His Leu His Asn Asn Arg Ile His Ser
    210                 215                 220
Leu Gly Lys Lys Cys Phe Asp Gly Leu His Ser Leu Glu Thr Leu Asp
225                 230                 235                 240
Leu Asn Tyr Asn Asn Leu Asp Glu Phe Pro Thr Ala Ile Arg Thr Leu
                245                 250                 255
Ser Asn Leu Lys Glu Leu Gly Phe His Ser Asn Asn Ile Arg Ser Ile
            260                 265                 270
Pro Glu Lys Ala Phe Val Gly Asn Pro Ser Leu Ile Thr Ile His Phe
        275                 280                 285
Tyr Asp Asn Pro Ile Gln Phe Val Gly Arg Ser Ala Phe Gln His Leu
    290                 295                 300
Pro Glu Leu Arg Thr Leu Thr Leu Asn Gly Ala Ser Gln Ile Thr Glu
305                 310                 315                 320
Phe Pro Asp Leu Thr Gly Thr Ala Asn Leu Glu Ser Leu Thr Leu Thr
                325                 330                 335
Gly Ala Gln Ile Ser Ser Leu Pro Gln Thr Val Cys Asn Gln Leu Pro
            340                 345                 350
Asn Leu Gln Val Leu Asp Leu Ser Tyr Asn Leu Leu Glu Asp Leu Pro
        355                 360                 365
Ser Phe Ser Val Cys Gln Lys Leu Gln Lys Ile Asp Leu Arg His Asn
    370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
            420                 425                 430
Leu Leu Ser Ser Phe Pro Ile Thr Gly Leu His Gly Leu Thr His Leu
        435                 440                 445
Lys Leu Thr Gly Asn His Ala Leu Gln Ser Leu Ile Ser Ser Glu Asn
    450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Leu His Lys Lys Asp Ala Gly
            500                 505                 510
Met Phe Gln Ala Gln Asp Glu Arg Asp Leu Glu Asp Phe Leu Leu Asp
        515                 520                 525
Phe Glu Glu Asp Leu Lys Ala Leu His Ser Val Gln Cys Ser Pro Ser
    530                 535                 540
Pro Gly Pro Phe Lys Pro Cys Glu His Leu Leu Asp Gly Trp Leu Ile
545                 550                 555                 560
Arg Ile Gly Val Gly Arg Ala Asp Lys Thr His Thr Cys Pro Cys
                565                 570                 575
Pro Ala Pro Glu Leu Leu Gly Gly Pro Ser Val Phe Leu Phe Pro Pro
            580                 585                 590
Lys Pro Lys Asp Thr Leu Met Ile Ser Arg Thr Pro Glu Val Thr Cys
        595                 600                 605
```

-continued

```
Val Val Val Asp Val Ser His Glu Asp Pro Glu Val Lys Phe Asn Trp
    610             615                 620
Tyr Val Asp Gly Val Glu Val His Asn Ala Lys Thr Lys Pro Arg Glu
625             630                 635                 640
Glu Gln Tyr Asn Ser Thr Tyr Arg Val Val Ser Val Leu Thr Val Leu
                645                 650                 655
His Gln Asp Trp Leu Asn Gly Lys Glu Tyr Lys Cys Lys Val Ser Asn
            660                 665                 670
Lys Ala Leu Pro Ala Pro Ile Glu Lys Thr Ile Ser Lys Ala Lys Gly
            675                 680                 685
Gln Pro Arg Glu Pro Gln Val Tyr Thr Leu Pro Pro Ser Arg Asp Glu
690             695                 700
Leu Thr Lys Asn Gln Val Ser Leu Thr Cys Leu Val Lys Gly Phe Tyr
705             710                 715                 720
Pro Ser Asp Ile Ala Val Glu Trp Ser Asn Gly Gln Pro Glu Asn
                725                 730                 735
Asn Tyr Lys Thr Thr Pro Pro Val Leu Asp Ser Asp Gly Ser Phe Phe
            740                 745                 750
Leu Tyr Ser Lys Leu Thr Val Asp Lys Ser Arg Trp Gln Gln Gly Asn
            755                 760                 765
Val Phe Ser Cys Ser Val Met His Glu Ala Leu His Asn His Tyr Thr
    770                 775                 780
Gln Lys Ser Leu Ser Leu Ser Pro Gly Lys
785                 790

<210> SEQ ID NO 16
<211> LENGTH: 1482
<212> TYPE: DNA
<213> ORGANISM: Artificial Sequence
<220> FEATURE:
<223> OTHER INFORMATION: Synthetic RSPO1-Fc Antibody

<400> SEQUENCE: 16
atgcggcttg gcctgtgtgt ggtggccctg gttctgagct ggacgcacct caccatcagc      60
agccggggga tcaagggaa aaggcagagg cggatcagtg ccgagggag ccaggcctgt      120 gccaaaggct gtgagctctg ctctgaagtc aacggctgcc tcaagtgctc acccaagctg      180
ttcatcctgc tggagaggaa cgacatccgc caggtgggcg tctgcttgcc gtcctgccca      240
cctggatact cgacgcccg caaccccgac atgaacaagt gcatcaaatg caagatcgag      300
cactgtgagg cctgcttcag ccataacttc tgcaccaagt gtaaggaggg cttgtacctg      360
cacaagggcc gctgctatcc agcttgtccc gagggctcct cagctgccaa tggcaccatg      420
gagtgcagta gtcctgcgca atgtgaaatg agcgagtggt ctccgtgggg gccctgctcc      480
aagaagcagc agctctgtgg tttccggagg ggctccgagg agcggacacg cagggtgcta      540
catgcccctg tgggggacca tgctgcctgc tctgacacca aggagacccg gaggtgcaca      600
gtgaggagag tgccgtgtcc tgaggggcag aagaggagga agggaggcca gggccggcgg      660
gagaatgcca acaggaacct ggccaggaag gagagcaagg aggcggtgc tggctctcga      720 agacgcaagg ggcagcaaca gcagcagcag caaggggacag tggggccact cacatctgca      780
gggcctgccg ggcgcgccga caaaactcac acatgcccac cgtgcccagc acctgaactc      840 ctgggggggac cgtcagtctt cctcttcccc ccaaaaccca aggacaccct catgatctcc      900
cggacccctg aggtcacatg cgtggtggtg gacgtgagcc acgaagaccc tgaggtcaag      960
ttcaactggt acgtggacgg cgtggaggtg cataatgcca agacaaagcc gcgggaggag     1020
```

```
cagtacaaca gcacgtaccg tgtggtcagc gtcctcaccg tcctgcacca ggactggctg   1080
aatggcaagg agtacaagtg caaggtctcc aacaaagccc tcccagcccc catcgagaaa   1140
accatctcca agccaaagg gcagcccga gaaccacagg tgtacaccct gcccccatcc     1200
cgggatgagc tgaccaagaa ccaggtcagc ctgacctgcc tggtcaaagg cttctatccc   1260
agcgacatcg ccgtggagtg ggagagcaat gggcagccgg agaacaacta caagaccacg   1320
cctcccgtgc tggactccga cggctccttc ttcctctaca gcaagctcac cgtggacaag   1380
agcaggtggc agcaggggaa cgtcttctca tgctccgtga tgcatgaggc tctgcacaac   1440
cactacacac agaagagcct ctccctgtct ccgggtaaat ga                      1482
```

<210> SEQ ID NO 17
<211> LENGTH: 493
<212> TYPE: PRT
<213> ORGANISM: Artificial Sequence
<220> FEATURE:
<223> OTHER INFORMATION: Synthetic RSPO2-Fc Antibody

<400> SEQUENCE: 17

```
Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala Gly Arg Ala Asp Lys Thr His Thr Cys
            260                 265                 270

Pro Pro Cys Pro Ala Pro Glu Leu Leu Gly Gly Pro Ser Val Phe Leu
        275                 280                 285
```

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 18
<211> LENGTH: 1422
<212> TYPE: DNA
<213> ORGANISM: Artificial Sequence
<220> FEATURE:
<223> OTHER INFORMATION: Synthetic RSPO2-Fc Antibody

<400> SEQUENCE: 18
atgcagtttc gccttttctc ctttgccctc atcattctga actgcatgga ttacagccac      60
tgccaaggca accgatggag acgcagtaag cgagctagtt atgtatcaaa tcccatttgc     120
aagggttgtt tgtcttgttc aaaggacaat gggtgtagcc gatgtcaaca gaagttgttc     180
ttcttccttc gaagagaagg gatgcgccag tatggagagt gcctgcattc ctgcccatcc     240
gggtactatg gacaccgagc cccagatatg aacagatgtg caagatgcag aatagaaaac     300
tgtgattctt gctttagcaa agacttttgt accaagtgca agtaggcttt tatttgcat      360
agaggccgtt gctttgatga atgtccagat ggttttgcac cattagaaga aaccatggaa     420
tgtgtggaag atgtgaagt tggtcattgg agcgaatggg aacttgtag cagaaataat       480
cgcacatgtg gatttaaatg gggtctggaa accagaacac ggcaaattgt taaaaagcca     540
gtgaaagaca caatactgtg tccaaccatt gctgaatcca ggagatgcaa gatgacaatg     600
aggcattgtc caggagggaa gagaacacca aaggcgaagg agaagaggaa caagaaaaag     660
aaaaggaagc tgatagaaag ggcccaggag caacacagcg tcttcctagc tacagacaga     720
gctaaccaag ggcgcgccga caaaactcac acatgcccac cgtgcccagc acctgaactc     780
ctggggggac cgtcagtctt cctcttcccc ccaaaaccca aggacaccct catgatctcc     840
cggacccctg aggtcacatg cgtggtggtg gacgtgagcc acgaagaccc tgaggtcaag     900

-continued

```
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagccccga gaaccacagg tgtacaccct gccccatcc    1140 cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggctccttc ttcctctaca gcaagctcac cgtggacaag   1320
agcaggtggc agcaggggaa cgtcttctca tgctccgtga tgcatgaggc tctgcacaac   1380
cactacacac agaagagcct ctccctgtct ccgggtaaat ga                      1422
```

<210> SEQ ID NO 19
<211> LENGTH: 473
<212> TYPE: PRT
<213> ORGANISM: Artificial Sequence
<220> FEATURE:
<223> OTHER INFORMATION: Synthetic RSPO2-Fc Antibody

<400> SEQUENCE: 19

```
Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
            20                  25                  30

Ser Tyr Val Ser Asn Pro Ile Cys Lys Gly Cys Leu Ser Cys Ser Lys
        35                  40                  45

Asp Asn Gly Cys Ser Arg Cys Gln Gln Lys Leu Phe Phe Phe Leu Arg
    50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
        115                 120                 125

Pro Asp Gly Phe Ala Pro Leu Glu Glu Thr Met Glu Cys Val Glu Gly
    130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
        195                 200                 205

Thr Pro Lys Ala Lys Glu Lys Arg Asn Lys Lys Lys Arg Lys Leu
    210                 215                 220

Ile Glu Arg Ala Gln Glu Gln His Ser Val Phe Leu Ala Thr Asp Arg
225                 230                 235                 240

Ala Asn Gln Gly Arg Ala Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
```

```
                    275                 280                 285
Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 20
<211> LENGTH: 1509
<212> TYPE: DNA
<213> ORGANISM: Artificial Sequence
<220> FEATURE:
<223> OTHER INFORMATION: Synthetic RSPO3-Fc Antibody

<400> SEQUENCE: 20
atgcacttgc gactgatttc ttggcttttt atcattttga actttatgga atacatcggc      60
agccaaaacg cctcccgggg aaggcgccag cgaagaatgc atcctaacgt tagtcaaggc     120
tgccaaggag gctgtgcaac atgctcagat tacaatggat gtttgtcatg taagcccaga     180 ctatttttg ctctggaaag aattggcatg aagcagattg gagtatgtct ctcttcatgt     240
ccaagtggat attatggaac tcgatatcca gatataaata gtgtacaaa atgcaaagct     300 gactgtgata cctgtttcaa caaaaatttc tgcacaaaat gtaaaagtgg attttactta     360
cacctggaaa gtgccttgaa caattgccca gaagggttgg aagccaacaa ccatactatg     420
gagtgtgtca gtattgtgca ctgtgaggtc agtgaatgga atccttggag tccatgcacg     480
aagaagggaa aacatgtgg cttcaaaaga gggactgaaa cacgggtccg agaataata     540 cagcatcctt cagcaaaggg taacctgtgt cccccaacaa atgagacaag aaagtgtaca     600
gtgcaaagga agaagtgtca gaagggagaa cgaggaaaaa aggaaggga gaggaaaaga     660 aaaaaaccta ataaaggaga agtaaagaa gcaatacctg acagcaaaag tctggaatcc     720
agcaaagaaa tcccagagca acgagaaaac aaacagcagc agaagaagcg aaaagtccaa     780
gataaacaga atcggtatc agtcagcact gtacacgggc gcgccgacaa aactcacaca     840
tgcccaccgt gcccagcacc tgaactcctg gggggaccgt cagtcttcct cttccccca     900 aaacccaagg acaccctcat gatctcccgg acccctgagg tcacatgcgt ggtggtggac     960
```

```
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggagt acaagtgcaa ggtctccaac   1140 aaagcccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatcccagc gacatcgccg tggagtggga gagcaatggg   1320
cagccggaga caactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacacaga agagcctctc cctgtctccg   1500
ggtaaatga                                                             1509
```

<210> SEQ ID NO 21
<211> LENGTH: 502
<212> TYPE: PRT
<213> ORGANISM: Artificial Sequence
<220> FEATURE:
<223> OTHER INFORMATION: Synthetic RSPO3-Fc Antibody

<400> SEQUENCE: 21

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Lys Lys
                245                 250                 255

Arg Lys Val Gln Asp Lys Gln Lys Ser Val Ser Val Ser Thr Val His
            260                 265                 270
```

```
Gly Arg Ala Asp Lys Thr His Thr Cys Pro Pro Cys Pro Ala Pro Glu
            275                 280                 285

Leu Leu Gly Gly Pro Ser Val Phe Leu Phe Pro Pro Lys Pro Lys Asp
            290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 22
<211> LENGTH: 1395
<212> TYPE: DNA
<213> ORGANISM: Artificial Sequence
<220> FEATURE:
<223> OTHER INFORMATION: Synthetic RSPO4-Fc Antibody

<400> SEQUENCE: 22
atgcgggcgc cactctgcct gctcctgctc gtcgcccacg ccgtggacat gctcgccctg      60
aaccgaagga agaagcaagt gggcactggc ctggggggca actgcacagg ctgtatcatc     120
tgctcagagg agaacggctg ttccacctgc agcagagggc tcttcctgtt catccgccgg     180
gaaggcatcc gccagtacgg caagtgcctg cacgactgtc cccctgggta cttcggcatc     240
cgcggccagg aggtcaacag tgcaaaaaaa tgtggggcca cttgtgagag ctgcttcagc     300
caggacttct gcatccggtg caagaggcag ttttacttgt acaaggggaa gtgtctgccc     360
acctgcccgc cgggcacttt ggcccaccag aacacgggg agtgccaggg ggagtgtgaa     420
ctgggtccct ggggcggctg gagcccctgc acacacaatg aaagacctg cggctcggct     480 tggggcctgg agagccgggt acgagaggct ggccgggctg gcatgagga gcagccacc     540 tgccaggtgc tttctgagtc aaggaaatgt cccatccaga ggccctgccc aggagagagg     600
agccccggcc agaagaaggg caggaaggac cggcgcccac gcaaggacag gaagctggac     660
cgcaggctgg acgtgaggcc gcgccagccc ggcctgcagc ccgggcgcgc cgacaaaact     720
```

```
cacacatgcc caccgtgccc agcacctgaa ctcctggggg gaccgtcagt cttcctcttc    780 ccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
agcctgacct gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cacagaagag cctctccctg   1380
tctccgggta aatga                                                    1395

<210> SEQ ID NO 23
<211> LENGTH: 464
<212> TYPE: PRT
<213> ORGANISM: Artificial Sequence
<220> FEATURE:
<223> OTHER INFORMATION: Synthetic RSPO4-Fc Antibody

<400> SEQUENCE: 23
```

Met Arg Ala Pro Leu Cys Leu Leu Leu Leu Val Ala His Ala Val Asp
1               5                   10                  15

Met Leu Ala Leu Asn Arg Arg Lys Lys Gln Val Gly Thr Gly Leu Gly
            20                  25                  30

Gly Asn Cys Thr Gly Cys Ile Ile Cys Ser Glu Glu Asn Gly Cys Ser
        35                  40                  45

Thr Cys Gln Gln Arg Leu Phe Leu Phe Ile Arg Arg Glu Gly Ile Arg
    50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro Gly Arg Ala Asp Lys Thr
225                 230                 235                 240

His Thr Cys Pro Pro Cys Pro Ala Pro Glu Leu Leu Gly Gly Pro Ser

```
                       245                 250                 255
Val Phe Leu Phe Pro Pro Lys Pro Lys Asp Thr Leu Met Ile Ser Arg
                    260                 265                 270

Thr Pro Glu Val Thr Cys Val Val Asp Val Ser His Glu Asp Pro
                275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
    450                 455                 460

<210> SEQ ID NO 24
<211> LENGTH: 705
<212> TYPE: DNA
<213> ORGANISM: Artificial Sequence
<220> FEATURE:
<223> OTHER INFORMATION: Synthetic Anti-LGR5 antibody 88R20 light chain

<400> SEQUENCE: 24
atggtgttgc agacccaggt cttcatttct ctgttgctct ggatctctgg tgcctacggg      60
gatatcgtgc tgacccagag cccggcgacc ctgagcctgt ctccgggcga acgtgcgacc     120
ctgagctgca gcgagccag tctgtttct tctaattatc tggcttggta ccagcagaaa      180
ccaggtcaag caccgcgtct attaatttat gatgcttcta atcgtgcaac tggggtcccg     240
gcgcgtttta gcggctctgg atccggcacg gatttcaccc tgaccattag cagcctggaa     300
cctgaagact ttgcggttta ttattgccag cagatggatg attttcctat gacctttggc     360
cagggtacga agttgaaat taaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt               705

<210> SEQ ID NO 25
<211> LENGTH: 235
<212> TYPE: PRT
<213> ORGANISM: Artificial Sequence
```

<220> FEATURE:
<223> OTHER INFORMATION: Synthetic Anti-LGR5 antibody 88R20 light chain

<400> SEQUENCE: 25

```
Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Asn Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Met
            100                 105                 110

Asp Asp Phe Pro Met Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 26
<211> LENGTH: 1389
<212> TYPE: DNA
<213> ORGANISM: Artificial Sequence
<220> FEATURE:
<223> OTHER INFORMATION: Synthetic Anti-LGR5 antibody 88R20 heavy chain

<400> SEQUENCE: 26

```
atgaaacacc tgtggttctt cctcctgctg gtggcagctc ccagatgggt cctgtcccag    60
gtgcaattgg ttcagtctgg cgcggaagtg aaaaaaccgg gcagcagcgt gaaagtgagc   120
tgcaaagcct ccggaggcac ttttcttct tatgctattt cttgggtgcg ccaagcccct   180
gggcagggtc tcgagtggat gggcggtatc attccgattt ttggcatggc gaattacgcg   240
cagaagtttc agggccgggt gaccattacc gcggatgaaa gcaccagcac cgcgtatatg   300
gaactgagca gcctgcgtag cgaagatacg gccgtgtatt attgcgcgcg ttatgatttt   360
attactcatt ttgattttg gggccaaggc accctggtga cggttagctc agccagcaca   420
aagggcccta gcgtcttccc tctggctccc tgcagcagga gcaccagcga gagcacagcc   480
gccctgggct gcctggtcaa ggactacttc cccgaaccgg tgacggtgtc gtggaactca   540
ggcgctctga ccagcggcgt gcacaccttc ccagctgtcc tacagtcctc aggactctac   600
```

```
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc accgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg cagccccga   1080 gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                            1389

<210> SEQ ID NO 27
<211> LENGTH: 463
<212> TYPE: PRT
<213> ORGANISM: Artificial Sequence
<220> FEATURE:
<223> OTHER INFORMATION: Synthetic Anti-LGR5 antibody 88R20 heavy chain

<400> SEQUENCE: 27

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Met Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Tyr Asp Phe Ile Thr His Phe Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220
```

```
Lys Pro Ser Asn Thr Lys Val Asp Lys Thr Val Glu Arg Lys Cys Cys
225                 230                 235                 240

Val Glu Cys Pro Pro Cys Pro Ala Pro Val Ala Gly Pro Ser Val
            245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
                275                 280                 285

Val Gln Phe Asn Trp Tyr Val Asp Gly Val Glu Val His Asn Ala Lys
            290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
                450                 455                 460

<210> SEQ ID NO 28
<211> LENGTH: 708
<212> TYPE: DNA
<213> ORGANISM: Artificial Sequence
<220> FEATURE:
<223> OTHER INFORMATION: Synthetic Anti-LGR5 antibody 88R21 light chain

<400> SEQUENCE: 28
atggcctggg ctctgctgct cctcaccctc ctcactcagg gcacaggatc ctgggctgat    60
atcgcactga cccagccagc ttcagtgagc ggctcaccag gtcagagcat taccatctcg   120
tgtacgggta ctaacagcga tgttggtact tataattatg tgcattggta ccagcagcat   180
cccgggaagg cgccgaaact tatgatttat gatggttcta atcgtccctc aggcgtgagc   240
aaccgtttta gcggatccaa aagcggcaac accgcgagcc tgaccattag cggcctgcaa   300
gcggaagacg aagcggatta ttattgccag gcttatgatt ctcattcttt taatattgtg   360
tttggcggcg gcacgaagtt aaccgtccta ggtcagccca aggctgcccc ctcggtcact   420
ctgttcccgc cctcctctga ggagcttcaa gccaacaagg ccacactggt gtgtctcata   480
agtgacttct acccgggagc cgtgacagtg gcctggaagg cagatagcag ccccgtcaag   540
gcgggagtgg agaccaccac acctccaaaa caaagcaaca caagtacgc ggccagcagc   600 tatctgagcc tgacgcctga gcagtggaag tcccacagaa gctacagctg ccaggtcacg   660
catgaaggga gcaccgtgga agacagtg gcccctacag aatgttca                  708
```

<210> SEQ ID NO 29
<211> LENGTH: 236
<212> TYPE: PRT
<213> ORGANISM: Artificial Sequence
<220> FEATURE:
<223> OTHER INFORMATION: Synthetic Anti-LGR5 antibody 88R21 light chain

<400> SEQUENCE: 29

```
Met Ala Trp Ala Leu Leu Leu Thr Leu Leu Thr Gln Gly Thr Gly
1               5                   10                  15

Ser Trp Ala Asp Ile Ala Leu Thr Gln Pro Ala Ser Val Ser Gly Ser
            20                  25                  30

Pro Gly Gln Ser Ile Thr Ile Ser Cys Thr Gly Thr Asn Ser Asp Val
        35                  40                  45

Gly Thr Tyr Asn Tyr Val His Trp Tyr Gln Gln His Pro Gly Lys Ala
    50                  55                  60

Pro Lys Leu Met Ile Tyr Asp Gly Ser Asn Arg Pro Ser Gly Val Ser
65              70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Gln Ala Tyr
            100                 105                 110

Asp Ser His Ser Phe Asn Ile Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

<210> SEQ ID NO 30
<211> LENGTH: 1398
<212> TYPE: DNA
<213> ORGANISM: Artificial Sequence
<220> FEATURE:
<223> OTHER INFORMATION: Synthetic Anti-LGR5 antibody 88R21 heavy chain

<400> SEQUENCE: 30

```
atgaaacacc tgtggttctt cctcctgctg gtggcagctc ccagatgggt cctgtcccag    60
gtgcaattgg ttcagtctgg cgcggaagtg aaaaaaccgg gcagcagcgt gaaagtgagc   120
tgcaaagcct ccggacgcac ttttctaat tatgctattg gttgggtgcg ccaagccct    180 gggcagggtc tcgagtggat gggcggtatc cgtccgaatt ttggctgggc gaagtacgcg   240
cagaagtttc agggccgggt gaccattacc gcggatgaaa gcaccagcac cgcgtatatg   300
gaactgagca gcctgcgtag cgaagatacg gccgtgtatt attgcgcgcg ttatggtcag   360
ggtcattttc cttctgcttt tgattattgg ggccaaggca ccctggtgac ggttagctca   420
gccagcacaa agggccctag cgtcttccct ctggctccct gcagcaggag caccagcgag   480
```

```
agcacagccg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                  1398

<210> SEQ ID NO 31
<211> LENGTH: 466
<212> TYPE: PRT
<213> ORGANISM: Artificial Sequence
<220> FEATURE:
<223> OTHER INFORMATION: Synthetic Anti-LGR5 antibody 88R21 heavy chain

<400> SEQUENCE: 31

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Arg Thr Phe
        35                  40                  45

Ser Asn Tyr Ala Ile Gly Trp Val Arg Gln Ala Pro Gly Gln Gly Leu
    50                  55                  60

Glu Trp Met Gly Gly Ile Arg Pro Asn Phe Gly Trp Ala Lys Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Tyr Gly Gln Gly His Phe Pro Ser Ala Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

```
Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
        290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly Lys
465

<210> SEQ ID NO 32
<211> LENGTH: 12
<212> TYPE: PRT
<213> ORGANISM: Artificial Sequence
<220> FEATURE:
<223> OTHER INFORMATION: Synthetic Anti-LGR5 antibody 88R20 Light Chain
      CDR1

<400> SEQUENCE: 32

Arg Ala Ser Gln Ser Val Ser Ser Asn Tyr Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic Anti-LGR5 antibody 88R20 Light Chain
      CDR2

<400> SEQUENCE: 33

Asp Ala Ser Asn Arg Ala Thr
1               5
```

<210> SEQ ID NO 34
<211> LENGTH: 8
<212> TYPE: PRT
<213> ORGANISM: Artificial Sequence
<220> FEATURE:
<223> OTHER INFORMATION: Synthetic Anti-LGR5 antibody 88R20 Light Chain
      CDR3

<400> SEQUENCE: 34

Gln Gln Met Asp Asp Phe Pro Met
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Anti-LGR5 antibody 88R20 Heavy Chain
      CDR1

<400> SEQUENCE: 35

Ser Ser Tyr Ala Ile Ser
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic Anti-LGR5 antibody 88R20 Heavy Chain
      CDR2

<400> SEQUENCE: 36

Gly Ile Ile Pro Ile Phe Gly Met Ala Asn Tyr Ala Gln Lys Phe Gln
1               5                   10                  15

Gly

<210> SEQ ID NO 37
<211> LENGTH: 9
<212> TYPE: PRT
<213> ORGANISM: Artificial Sequence
<220> FEATURE:
<223> OTHER INFORMATION: Synthetic Anti-LGR5 antibody 88R20 Heavy Chain
      CDR3

<400> SEQUENCE: 37

Tyr Asp Phe Ile Thr His Phe Asp Phe
1               5

<210> SEQ ID NO 38
<211> LENGTH: 14
<212> TYPE: PRT
<213> ORGANISM: Artificial Sequence
<220> FEATURE:
<223> OTHER INFORMATION: Synthetic Anti-LGR5 antibody 88R21 Light Chain
      CDR1

<400> SEQUENCE: 38

Thr Gly Thr Asn Ser Asp Val Gly Thr Tyr Asn Tyr Val His
1               5                   10

<210> SEQ ID NO 39
<211> LENGTH: 8
<212> TYPE: PRT
<213> ORGANISM: Artificial Sequence
<220> FEATURE:
<223> OTHER INFORMATION: Synthetic Anti-LGR5 antibody 88R21 Light Chain
      CDR2

<400> SEQUENCE: 39

Asp Gly Ser Asn Arg Pro Ser Gly
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic Anti-LGR5 antibody 88R21 Light Chain
      CDR3

<400> SEQUENCE: 40

Gln Ala Tyr Asp Ser His Ser Phe Asn Ile
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Synthetic Anti-LGR5 antibody 88R21 Heavy Chain
      CDR1

<400> SEQUENCE: 41

Ser Asn Tyr Ala Ile Gly
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic Anti-LGR5 antibody 88R21 Heavy Chain
      CDR2

<400> SEQUENCE: 42

Gly Ile Arg Pro Asn Phe Gly Trp Ala Lys Tyr Ala Gln Lys Phe Gln
1               5                   10                  15

Gly

<210> SEQ ID NO 43
<211> LENGTH: 12
<212> TYPE: PRT
<213> ORGANISM: Artificial Sequence
<220> FEATURE:
<223> OTHER INFORMATION: Synthetic Anti-LGR5 antibody 88R21 Heavy Chain
      CDR3

<400> SEQUENCE: 43

Tyr Gly Gln Gly His Phe Pro Ser Ala Phe Asp Tyr
1               5                   10

<210> SEQ ID NO 44
<211> LENGTH: 110
<212> TYPE: PRT
<213> ORGANISM: Artificial Sequence
<220> FEATURE:
<223> OTHER INFORMATION: Synthetic anti-LGR5 antibody 88R20 Light Chain

<400> SEQUENCE: 44

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

```
Tyr Leu Ala Trp Tyr Gln Gln Lys Pro Gly Gln Ala Pro Arg Leu Leu
            35                  40                  45

Ile Tyr Asp Ala Ser Asn Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Met Asp Asp Phe Pro
                 85                  90                  95

Met Thr Phe Gly Gln Gly Thr Lys Val Glu Ile Lys Arg Thr
            100                 105                 110

<210> SEQ ID NO 45
<211> LENGTH: 118
<212> TYPE: PRT
<213> ORGANISM: Artificial Sequence
<220> FEATURE:
<223> OTHER INFORMATION: Synthetic anti-LGR5 antibody 88R20 Heavy Chain

<400> SEQUENCE: 45

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Met Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Phe Ile Thr His Phe Asp Phe Trp Gly Gln Gly Thr
            100                 105                 110

Leu Val Thr Val Ser Ser
        115

<210> SEQ ID NO 46
<211> LENGTH: 112
<212> TYPE: PRT
<213> ORGANISM: Artificial Sequence
<220> FEATURE:
<223> OTHER INFORMATION: Synthetic anti-LGR5 Antibody 88R21 Light Chain

<400> SEQUENCE: 46

Asp Ile Ala Leu Thr Gln Pro Ala Ser Val Ser Gly Ser Pro Gly Gln
 1               5                  10                  15

Ser Ile Thr Ile Ser Cys Thr Gly Thr Asn Ser Asp Val Gly Thr Tyr
             20                  25                  30

Asn Tyr Val His Trp Tyr Gln Gln His Pro Gly Lys Ala Pro Lys Leu
         35                  40                  45

Met Ile Tyr Asp Gly Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ala Tyr Asp Ser His
                 85                  90                  95

Ser Phe Asn Ile Val Phe Gly Gly Gly Thr Lys Leu Thr Val Leu Gly
            100                 105                 110
```

```
<210> SEQ ID NO 47
<211> LENGTH: 121
<212> TYPE: PRT
<213> ORGANISM: Artificial Sequence
<220> FEATURE:
<223> OTHER INFORMATION: Synthetic anti-LGR5 Antibody 88R21 Heavy Chain

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Arg Thr Phe Ser Asn Tyr
            20                  25                  30

Ala Ile Gly Trp Val Arg Gln Ala Pro Gly Gln Gly Leu Glu Trp Met
        35                  40                  45

Gly Gly Ile Arg Pro Asn Phe Gly Trp Ala Lys Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Gln Gly His Phe Pro Ser Ala Phe Asp Tyr Trp Gly
            100                 105                 110

Gln Gly Thr Leu Val Thr Val Ser Ser
            115                 120
```

COMPOSITIONS AND METHODS FOR TREATING AND DIAGNOSING CANCER

CROSS-REFERENCE TO RELATED APPLICATIONS

This application claims the priority benefit of U.S. provisional application No. 60/947,611, filed Jul. 2, 2007, which is hereby incorporated by reference herein in its entirety.

BACKGROUND OF THE INVENTION

1. Field of the Invention

The present invention relates to the field of oncology and provides novel compositions and methods for diagnosing and treating cancer. In particular, the invention provides the means and methods for characterizing, studying, diagnosing, providing a prognosis, and treating cancers comprising solid tumor cancer stem cells.

2. Background Art

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them—breast, lung, colorectal, and prostate—account for over half of all new cases (Jemal et al., 2003, Cancer J. Clin. 53:5-26).

Breast cancer is the most common cancer in woman, with an estimate 12% of women at risk of developing the disease during their lifetime. Although mortality rates have decreased due to earlier detection and improved treatments, breast cancer remains a leading cause of death in middle-aged women. Furthermore, metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. And although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris, J R: "Staging of breast carcinoma" in Harris, J. R., Hellman, S., Henderson, I. C., Kinne D. W. (eds.): Breast Diseases. Philadelphia, Lippincott, 1991. These parameters are used to provide a prognosis and select an appropriate therapy. The morphologic appearance of the tumor may also be assessed but because tumors with similar histopathologic appearance can exhibit significant clinical variability, this approach has serious limitations. Finally, assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death (Jemal et al., 2003, CA Cancer J. Clin. 53:5-26). Since the introduction of the prostate specific antigen (PSA) blood test, early detection of prostate cancer has dramatically improved survival rates, and the five year survival rate for patients with local and regional stage prostate cancers at the time of diagnosis is nearing 100%. Yet more than 50% of patients will eventually develop locally advanced or metastatic disease (Muthuramalingam et al., 2004, Clin. Oncol. 16:505-16).

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used (Muthuramalingam et al., 2004, Clin. Oncol. 16:505-16; Trojan et al., 2005, Anticancer Res. 25:551-61).

Lung cancer is the most common cancer worldwide, the third most commonly diagnosed cancer in the United States, and by far the most frequent cause of cancer deaths (Spiro et al., 2002, Am. J. Respir. Crit. Care Med. 166:1166-96; Jemal et al., 2003, CA Cancer J. Clin. 53:5-26). Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early and often. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years (Spiro et al., 2002, Am. J. Respir. Crit. Care Med. 166:1166-96).

Colorectal cancer is the third most common cancer and the fourth most frequent cause of cancer deaths worldwide (Weitz et al., 2005, Lancet 365:153-65). Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and elsewhere by lymphatic, hematogenous, transperitoneal, and perineural spread. The most common site of extralymphatic involvement is the liver, with the lungs the most frequently affected extra-abdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through muscularis propria and can penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients.

Epithelial carcinomas of the head and neck arise from the mucosal surfaces in the head and neck area and are typically squamous cell in origin. This category includes tumors of the paranasal sinuses, the oral cavity, and the nasopharynx, oropharynx, hypopharynx, and larynx.

The annual number of new cases of head and neck cancers in the United States is approximately 40,000 per year, accounting for about 5 percent of adult malignancies. Head and neck cancers are more common in some other countries, and the worldwide incidence probably exceeds half a million cases annually. In North American and Europe, the tumors usually arise from the oral cavity, oropharynx, or larynx, whereas nasopharyngeal cancer is more common in the Mediterranean countries and in the Far East.

Traditional modes of therapy (radiation therapy, chemotherapy, and hormonal therapy), while useful, have been limited by the emergence of treatment-resistant cancer cells. Clearly, new approaches are needed to identify targets for treating head and neck cancer and cancer generally.

Cancer arises from dysregulation of the mechanisms that control normal tissue development and maintenance, and increasingly stem cells are thought to play a central role (Beachy et al., 2004, Nature 432:324). During normal animal development, cells of most or all tissues are derived from normal precursors, called stem cells (Morrison et al., 1997, Cell 88:287-98; Morrison et al., 1997, Curr. Opin. Immunol. 9:216-21; Morrison et al., 1995, Annu. Rev. Cell. Dev. Biol. 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-known example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., 1998, Genes, Chromosomes & Cancer 12:122-129; Kuukasjrvi et al., 1997, Cancer Res. 57:1597-1604; Bonsing et al., 1993, Cancer 71:382-391; Bonsing et al., 2000, Genes Chromosomes & Cancer 82: 173-183; Beerman H et al., 1991, Cytometry. 12:147-54; Aubele M & Werner M, 1999, Analyt. Cell. Path. 19:53; Shen L et al., 2000, Cancer Res. 60:3884).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell division. In this stem cell model, solid tumors contain a distinct and limited (possibly even rare) subset of cells that share properties with normal "stem cells" in that they extensively proliferate and efficiently give rise both to additional solid tumor stem cells (self-renewal) and to the majority of within a solid tumor that lack tumorigenic potential. Indeed, mutations within a long-lived stem cell population can initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, Nature 17:645-8). More recently it has been demonstrated that malignant human breast tumors similarly harbor a small, distinct population of cancer stem cells enriched for the ability to form tumors in immunodeficient mice. An ESA+, CD44+, CD24-/low, Lin-cell population was found to be 50-fold enriched for tumorigenic cells compared to unfractionated tumor cells (Al-Hajj et al., 2003, PNAS 100:3983-8). Furthermore, a similar population is also present in colon cancers. The ability to prospectively isolate the tumorigenic cancer cells has permitted precise investigation of critical biological pathways that underlie tumorigenicity in these cells, and thus promises the development of better diagnostic assays and therapeutics for cancer patients. It is toward this purpose and the other purposes described herein that this invention is directed.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

BRIEF SUMMARY OF THE INVENTION

The present invention relates to compositions and methods in the field of oncology. In particular, the present invention is based, in part, on the discovery that an LGR (leucine-rich repeat-containing, G protein-coupled receptor) protein, such as LGR5 (leucine-rich repeat-containing, G protein-coupled receptor 5) is a protein over-expressed in solid tumor cancer stem cells, and thus is a cancer stem cell marker useful in the characterization, study, diagnosis, and treatment of cancer. The present invention further identifies an interaction between the R-spondin RSPO1 and LGR5 as an alternative pathway for the activation of beta-catenin signaling, suggesting functional blocking of LGR5 can inhibit tumor growth. Interactions between LGR5 and each of the additional RSPO proteins RSPO2, RSPO3, and RSPO4 have now likewise been identified.

As such, in certain embodiments, the present invention provides biomolecules that disrupt functional signaling via a LGR protein, including, in certain embodiments, molecules that inhibit the interaction between R-spondin (RSPO) proteins and an LGR protein such as LGR5. In certain embodiments, the biomolecules are antibodies. For instance, in certain embodiments, the biomolecules may be antibodies that specifically bind to the extracellular domain of at least one human LGR protein. In certain embodiments, the present invention provides antibodies that specifically bind to an extracellular domain of a human LGR protein and inhibit growth of tumor cells. In certain embodiments, the LGR protein is LGR5. The present invention further provides methods of treating cancer comprising cancer stem cells. In certain embodiments, the method of treating cancer comprises administering a therapeutically effective amount of an antibody that specifically binds an extracellular domain of a LGR protein. In certain embodiments, the LGR protein is LGR5. The present invention further provides for a method of treating cancer in a human and/or inhibiting growth of a tumor in a human comprising administering to the human a therapeutically effective amount of an agent that (a) disrupts the binding of a human RSPO protein to a human LGR protein and/or (b) disrupts RSPO activation of LGR signaling. In some embodiments, the agent is an antibody. In certain embodiments, the agent binds a human LGR protein. In certain alternative embodiments, the agent is an antibody that specifically binds to the extracellular domain of at least one human LGR protein. In certain alternative embodiments, the agent is an antibody that specifically binds to the extracellular domain of two or more human LGR proteins In certain embodiments, the LGR protein is LGR5. In certain embodiments, the cancer or tumor comprises cancer stem cells.

In addition, the present invention provides a method of inhibiting beta-catenin signaling in a tumor cell, comprising contacting the tumor cell with an agent that (a) disrupts the binding of a human RSPO protein to a human LGR protein and/or (b) disrupts RSPO activation of LGR signaling. In certain embodiments, the agent binds a human LGR protein. In certain alternative embodiments, the agent is an antibody that specifically binds to the extracellular domain of at least one human LGR protein. In certain alternative embodiments, the agent is an antibody that specifically binds to the extracellular domain of two or more human LGR proteins. In certain embodiments, the LGR protein is LGR5. In certain embodiments, the method is an in vitro method. In certain embodiments, the method is an in vivo method.

The present invention further provides antibodies that bind to an extracellular domain of a human LGR protein and are capable of inhibiting growth of a solid tumor (e.g., a solid tumor comprising solid tumor stem cells) by (a) disrupting binding of a human RSPO protein to a human LGR protein; (b) disrupt RSPO activation of LGR signaling; and/or (c) inhibiting beta-catenin signaling. The present invention also provides antibodies that (a) bind to an extracellular domain of a human LGR protein; (b) disrupt binding of a human RSPO protein to a human LGR protein; (c) disrupt RSPO activation of LGR signaling; (d) inhibit beta-catenin signaling; and/or (e) are capable of inhibiting growth of a solid tumor (e.g., a solid tumor comprising solid tumor stem cells). In certain embodiments, the antibodies specifically bind to the extracellular domain of a human LGR protein. In certain embodiments, the human LGR protein is LGR5. In certain embodiments, the human RSPO protein is RSPO1. In some alternative embodiments, the human RSPO protein is RSPO2, RSPO3, or RSPO4. Cell lines producing the antibodies and compositions comprising the antibodies are further provided. Methods of using therapeutically effective amounts of compositions comprising the antibodies for treating cancer, including, but not limited to, by inhibiting growth of a tumor, are further provided. Methods using the antibodies, in vivo or in vitro, to inhibit beta-catenin signaling are also provided.

The invention further provides a monoclonal anti-LGR5 antibody 88M1 produced by a hybridoma cell line deposited on Jul. 2, 2008, with the American Type Culture collection (ATCC), located at 10801 University Blvd, Manassas, Va., 20110, USA, in accordance with the Budapest Treaty, having ATCC deposit number PTA-9342, deposited Jul. 2, 2008. Antibodies are also provided that specifically bind LGR5 and (a) comprise a heavy chain variable region and/or a light chain variable region having at least about 95% sequence identity to the heavy chain variable region and/or the light chain variable region (respectively) of 88M1; (b) comprise the heavy chain and/or light chain CDRs of 88M1; (c) bind to an epitope capable of binding 88M1; and/or (d) compete with 88M1 in a competitive binding assay. Cells lines producing the antibodies (including, but not limited to, the hybridoma cell line having ATCC deposit number PTA-9342, deposited Jul. 2, 2008) and compositions comprising the antibodies are further provided. Methods of using therapeutically effective amounts of compositions comprising the antibodies for treating cancer, including, but not limited to, by inhibiting growth of a tumor, are further provided. Methods using the antibodies, in vivo or in vitro, to inhibit beta-catenin signaling are also provided.

The invention further provides an antibody that binds LGR5, comprising: (a) a heavy chain CDR1 comprising SSYAIS (SEQ ID NO:35), a heavy chain CDR2 comprising GIIPIFGMANYAQKFQG (SEQ ID NO:36), and/or a heavy chain CDR3 comprising YDFITHFDF (SEQ ID NO:37); and/or (b) a light chain CDR1 comprising RASQSVSSNYLA (SEQ ID NO:32), a light chain CDR2 comprising DASNRAT (SEQ ID NO:33), and/or a light chain CDR3 comprising QQMDDFPM (SEQ ID NO:34). Polynucleotides comprising a polynucleotide encoding a heavy chain or light chain variable region of the antibody are further provided. Vectors and cells comprising the polynucleotides or antibodies are also provided, as are methods of treating cancer and/or inhibiting tumor growth in a human comprising administering a therapeutically effective amount of the antibody to the human. In some embodiments, the cancer or tumor comprises cancer stem cells.

The invention further provides an antibody that binds LGR5, comprising: (a) a heavy chain CDR1 comprising SNYAIG (SEQ ID NO:41), a heavy chain CDR2 comprising GIRPNFGWAKYAQKFQG (SEQ ID NO:42), and/or a heavy chain CDR3 comprising YGQGHFPSAFDY (SEQ ID NO:43); and/or (b) a light chain CDR1 comprising TGTNSDVGTYNYVH (SEQ ID NO:38), a light chain CDR2 comprising DGSNRPSG (SEQ ID NO:39), and/or a light chain CDR3 comprising QAYDSHSFNI (SEQ ID NO:40). Polynucleotides comprising a polynucleotide encoding a heavy chain or light chain variable region of the antibody are further provided. Vectors and cells comprising the polynucleotides or antibodies are also provided, as are methods of treating cancer and/or inhibiting tumor growth in a human comprising administering a therapeutically effective amount of the antibody to the human. In some embodiments, the cancer or tumor comprises cancer stem cells.

The invention further provides an antibody that binds LGR5, comprising: (a) a heavy chain variable region having at least about 80% sequence identity to SEQ ID NO:45; and/or (b) a light chain variable region having at least about 80% sequence identity to SEQ ID NO:44. Polynucleotides comprising a polynucleotide encoding such heavy chain or light chain variable regions are also provided. Vectors and cells comprising the polynucleotides or antibodies are also provided, as are methods of treating cancer and/or inhibiting tumor growth in a human comprising administering a therapeutically effective amount of the antibody to the human. In some embodiments, the cancer or tumor comprises cancer stem cells.

The invention further provides an antibody that binds LGR5, comprising: (a) a heavy chain variable region having at least about 80% sequence identity to SEQ ID NO:47; and/or (b) a light chain variable region having at least about 80% sequence identity to SEQ ID NO:46. Polynucleotides comprising a polynucleotide encoding such heavy chain or light chain variable regions are also provided. Vectors and cells comprising the polynucleotides or antibodies are also provided, as are methods of treating cancer and/or inhibiting tumor growth in a human comprising administering a therapeutically effective amount of the antibody to the human. In some embodiments, the cancer or tumor comprises cancer stem cells.

The present invention further provides methods of identifying and/or isolating cancer stem cells (e.g., based on expression of LGR5), screening for anti-cancer agents, and screening patients for suitability for treatment with the agents described herein.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

DETAILED DESCRIPTION OF THE INVENTION

Figure 1:
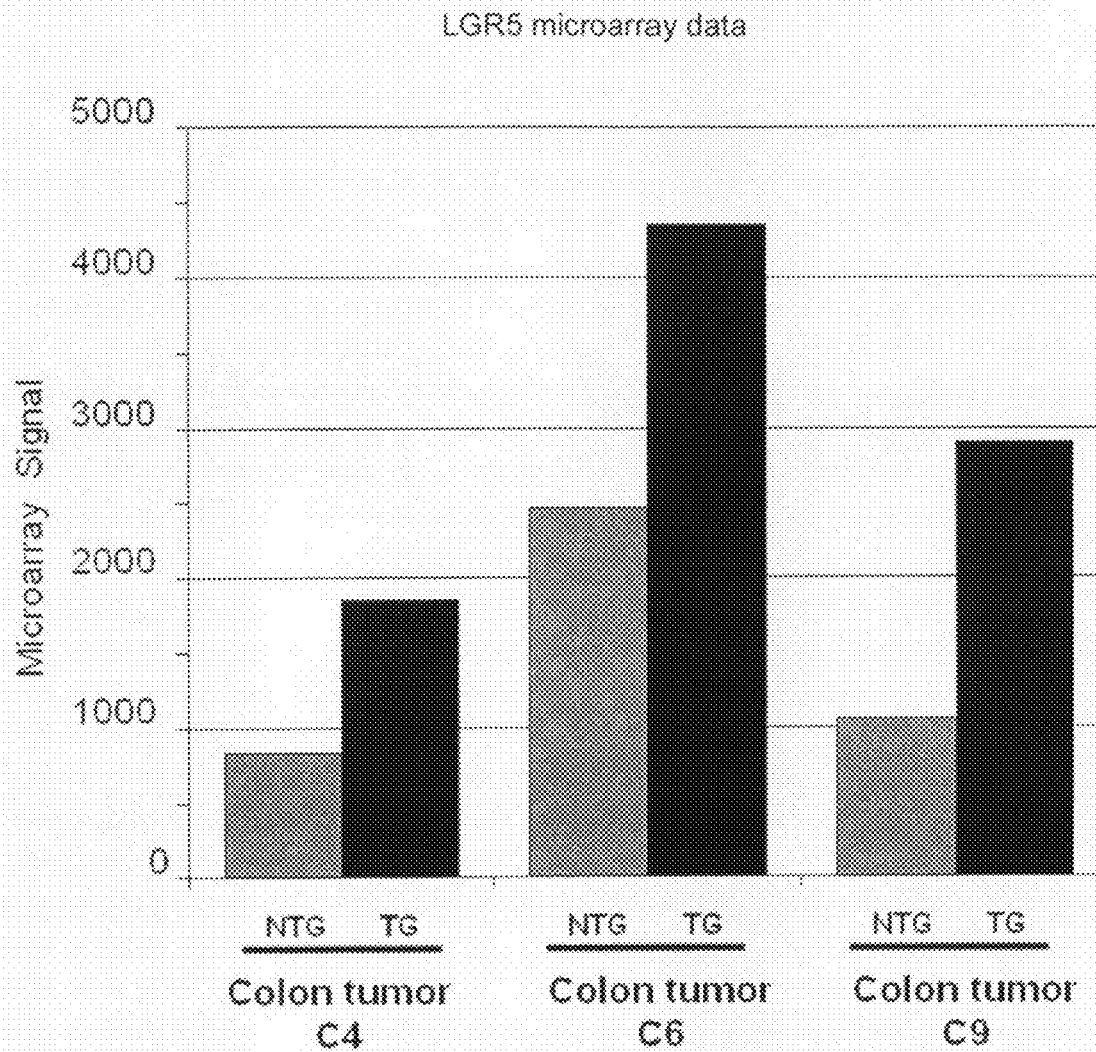
FIG. 1. LGR5 Is Overexpressed In Solid Tumor Cancer Stem Cells. Cells from human colon tumors were sorted by FACS into a tumorigenic "TG" fraction (right bars) containing cancer stem cells and a non-tumorigenic "NTG" fraction (left bars). mRNA was isolated from these fraction and microarray data was generated. LGR5 demonstrated higher mRNA expression in the TG cancer stem cell fraction from three independent human colon tumors (right bar of each set).

The present invention provides compositions and methods for characterizing, studying, diagnosing, and treating cancer. In particular, the present invention provides LGR5 as a marker of solid tumor cancer stem cells and identifies a novel interaction between LGR5 and an RSPO protein, RSPO1, (as well as RSPO2, RSPO3, and RSPO4) as an alternative pathway for the activation of beta-catenin signaling. Manipulation of this LGR5 signaling pathway, including disruption of functional LGR5 signaling, provides novel compositions and methods for the treatment of cancer.

This invention is based in part on the discovery of solid tumor stem cells (also referred to as cancer stem cells or solid tumor cancer stem cells) as a distinct and limited subset of cells within the heterogenous cell population of established solid tumors. These cancer stem cells share the properties of normal stem cells in that they extensively proliferate and efficiently give rise both to additional solid tumor stem cells (self-renewal) and to the majority of tumor cells of a solid tumor that lack tumorigenic potential. Identification of cancer stem cells relies both on 1) their expression of a unique pattern of cell-surface receptors used to isolate them from the bulk of non-tumorigenic tumor cells and 2) their properties of self-renewal and proliferation as assessed in xenograft animal models.

In certain embodiments, the invention thus provides a method for selectively targeting diagnostic or therapeutic agents to cancer stem cells. In certain embodiments, the invention also provides an agent, such as a biomolecule, that is selectively targeted to cancer stem cells (e.g. directed to one of the colon cancer stem cell cancer markers disclosed herein). In certain embodiments, the stem cell cancer marker targeted is part of a self-renewal or cell survival pathway. In certain embodiments, the present invention provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients (e.g., as an adjunct for mammography).

Additional guidance regarding cancer stem cells is provided in Published PCT patent application WO 02/12447 by the Regents of the University of Michigan and PCT patent application PCT/US02/39191 by the Regents of the University of Michigan, both of which are incorporated herein by reference.

The present invention identifies cancer stem cell expression as comprising elevated levels of LGR5 (leucine-rich repeat-containing G protein-coupled receptor 5) compared to non-tumorigenic tumor cells. LGR5 is a member of a small family of orphan seven transmembrane domain proteins with relatively large extracellular domains that includes LGR4, LGR5, and LGR6.

The present invention further identifies an interaction between RSPO1 and LGR5 that activates an alternative beta-catenin signaling pathway. R-spondins (RSPO) are a family of four small secreted proteins that have recently been recognized to stimulate beta-catenin in a manner similar to Wnt signaling. Interestingly, Wnt and RSPO proteins show profound synergism. Recently RSPO activation of beta-catenin has been suggested to be mediated through members of the Frizzled receptor family and the LRP5,6 co-receptor family (Nam et al., 2006, JBC 281:13247-57). The present invention identifies LGR5 as a receptor for RSPO.

The Wnt signaling pathway has long been implicated in cancer due to the presence of mutations activating the pathway in certain tumors (e.g. APC mutations in colon cancer) and the ability of certain WNTs to drive cancer when expressed as constitutive transgenes or following retroviral insertion (e.g. the wWnt1 breast tumor model). However, actual proof that the Wnt proteins themselves drive any spontaneous human tumors has proven surprisingly elusive.

The present invention identifies an alternative pathway via RSPO proteins and LGR proteins that can lead to activated beta-catenin in tumor cells. Without being bound by theory, the model suggests that the members of the LGR receptor family may function as a "rheostat" that gates the level of beta-catenin in response to Wnt due to the observed profound synergism demonstrated by R-spondin and Wnt in inducing beta-catenin. Because tumors exhibit markedly elevated levels of LGR5, they may consequently demonstrate elevated beta-catenin in the face of "normal" levels of Wnt proteins.

Based in part on these discoveries, the prevent invention provides, in certain embodiments, agents that disrupt the binding of at least one human RSPO protein to at least one LGR protein (e.g., LGR5). In certain embodiments, the agents disrupt RSPO activation of LGR signaling. In further embodiments, the agents inhibit tumor growth, including the growth of solid tumors comprising cancer stem cells. In some embodiments, the agents are antibodies that specifically bind at least one LGR protein. In some embodiments, the agents are antibodies that specifically bind two or more LGR proteins. Compositions comprising these agents and their use in the treatment of cancers (especially, but not limited to, those involving cancer stem cells) are further provided.

Other features, objects, and advantages of the invention will be apparent from the detailed description below.

Definitions

To facilitate an understanding of the present invention, a number of terms and phrases are defined below:

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

That an antibody "specifically binds" to or shows "specific binding" towards an epitope means that the antibody reacts or associates more frequently, more rapidly, with greater duration, and/or with greater affinity with the epitope than with alternative substances. As used herein, "specifically binds" means that an antibody binds to a protein with a $K_D$ of at least about 0.1 mM, at least about 1 μM, at least about 0.1 μM or better, or 0.01 μM or better. It is understood that an antibody or binding moiety that specifically binds to a first target may or may not specifically bind to a second target. As such, "specific binding" does not necessarily require (although it can include) exclusive binding, i.e. binding to a single target. Generally, but not necessarily, reference to binding means specific binding.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "receptor binding domain" refers to any native ligand for a receptor, including cell adhesion molecules, or any region or derivative of such native ligand retaining at least a qualitative receptor binding ability of a corresponding native ligand.

As used herein, the term "antibody-immunoadhesin chimera" comprises a molecule that combines at least one binding domain of an antibody with at least one immunoadhesin. Examples include, but are not limited to, the bispecific CD4-IgG chimeras described in Berg et al., PNAS (USA) (1991) and Charnow et al., J. Immunol., 153:4268 (1994), both of which are hereby incorporated by reference.

"Enriched", as in an enriched population of cells, can be defined phenotypically based upon the increased number of cells having a particular marker (e.g. as shown in Table 1) in a fractionated set of cells as compared with the number of cells having the marker in the unfractionated set of cells. However, the term "enriched" can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. The stem cell cancer markers of the present invention can be used to generate enriched populations of cancer stem cells. In some embodiments, the stem cell population is enriched at least 1.4 fold relative to unfractionated tumor cells. In other embodiments, the stem cell population is enriched 2 fold to 10 fold relative to unfractionated tumor cells. In further embodiments, the stem cell population is enriched 20 fold relative to unfractionated tumor cells.

"Isolated" in regard to cells, refers to a cell that is removed from its natural environment (such as in a solid tumor) and that is isolated or separated, and is at least about 30%, 50%, 75% free, or about 90% free, from other cells with which it is naturally present, but which lack the marker based on which the cells were isolated. The stem cell cancer markers of the present invention can be used to generate isolated populations of cancer stem cells.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; (3) are capable of symmetric cell divisions for self-renewal or self-maintenance; and, (4) are capable of forming palpable tumors upon serial transplantation in a xenograft model. The properties of enhanced proliferative capacity and asymmetric and symmetric cell division of "cancer stem cells", "tumor stem cells" or "solid tumor stem cells" confer on those cancer stem cells the ability to form palpable tumors upon serial transplantation into an immunocompromised mouse compared to the majority of tumor cells that fail to generate tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on the cancer stem cells of this invention the ability to form palpable tumors upon serial transplantation into an immunocompromised mouse compared to the majority of tumor cells that are unable to form tumors upon serial transplantation. Tumor cells, i.e. non-tumorigenic tumor cells, may form a tumor upon transplantation into an immunocompromised mouse a limited number of times (for example one or two times) after obtaining the tumor cells from a solid tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "unfractionated tumor cells", "presorted tumor cells", "bulk tumor cells", and their grammatical equivalents are used interchangeably to refer to a tumor cell population isolated from a patient sample (e.g. a tumor biopsy or pleural effusion) that has not been segregated, or fractionated, based on cell surface marker expression.

As used herein, the terms "non-ESA+CD44+ tumor cells", "non-ESA+44+". "sorted non-tumorigenic tumor cells", "non-stem cells" and their grammatical equivalents are used interchangeably to refer to a tumor population from which ESA+CD44+ cancer stem cells have been segregated, or removed, based on cell surface marker expression.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "high levels", "increased levels", "high expression", "increased expression", "elevated levels" or "upregulated expression" in regards to gene expression are used herein interchangeably to refer to expression of a gene in a cell or population of cells, particularly a cancer stem cell or population of cancer stem cells, at levels higher than the expression of that gene in a second cell or population of cells, for example, unfractionated colon tumor cells or non-ESA+44+ colon tumor cells. "Elevated levels" of gene expression refers to expression of a gene in a cancer stem cell or population of cancer stem cells at levels twice that or more of expression levels of the same gene in unfractionated colon tumor cells or non-ESA+44+ colon tumor cells. "Elevated levels" of gene expression also refers to expression of a gene in a cancer stem cell or population of cancer stem cells at levels six times that or more of expression levels of the same gene in unfractionated colon tumor cells or non-ESA+44+ colon tumor cells. "Elevated levels" of gene expression can be determined by detecting increased amounts of a polynucleotide (mRNA, cDNA, etc.) in cancer stem cells compared to unfractionated colon tumor cells or non-ESA+44+ colon tumor cells by, for example, quantitative RT-PCR or microarray analysis. Alternatively "elevated levels" of gene expression can be determined by detecting increased amounts of a protein in cancer stem cells compared to unfractionated colon tumor cells or non-ESA+44+ colon tumor cells by, for example, ELISA, Western blot, quantitative immunofluorescence.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, or immunofluorescence.

As used herein, the terms "low levels", "decreased levels", "low expression", "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example unfractionated colon tumor cells or non-ESA+44+ colon tumor cells. "Low levels" of gene expression refers to expression of a gene in a cancer stem cell or population of cancer stem cells at levels: 1) half that or below expression levels of the same gene in unfractionated colon tumor cells or non-ESA+44+ colon tumor cells and 2) at the lower limit of detection using conventional techniques. "Low levels" of gene expression can be determined by detecting decreased to nearly undetectable amounts of a polynucleotide (mRNA, cDNA, etc.) in cancer stem cells compared to unfractionated colon tumor cells or non-ESA+44+ colon tumor cells by, for example, quantitative RT-PCR or microarray analysis. Alternatively "low levels" of gene expression can be determined by detecting decreased to nearly undetectable amounts of a protein in cancer stem cells compared to unfractionated colon tumor cells or non-ESA+44+ colon tumor cells by, for example, ELISA, Western blot, or quantitative immunofluorescence.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous control" refers to measuring the level of expression of a gene (e.g., the level of mRNA or protein) relative to the level in a non-cancerous control sample. Gene expression can be measured using any suitable method, including but not limited to, those described herein.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer stem cells or for determining gene expression profile of that cancerous tissue. In some embodiment, biopsy tissue or fluid is obtained because a subject is suspected of having cancer. The biopsy tissue or fluid is then examined for the presence or absence of cancer, cancer stem cells, and/or cancer stem cell gene signature expression.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post-transcriptional cleavage and polyadenylation.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region can be present in a cDNA, genomic DNA or RNA form. When present in a DNA form, the oligonucleotide or polynucleotide can be single-stranded (i.e., the sense strand) or double-stranded. Suitable control elements such as enhancers/promoters, splice junctions, polyadenylation signals, etc. can be placed in close proximity to the coding region of the gene if needed to permit proper initiation of transcription and/or correct processing of the primary RNA transcript. Alternatively, the coding region utilized in the expression vectors of the present invention can contain endogenous enhancers/promoters, splice junctions, intervening sequences, polyadenylation signals, etc. or a combination of both endogenous and exogenous control elements.

As used herein the term "portion" when in reference to a nucleotide sequence (as in "a portion of a given nucleotide sequence") refers to fragments of that sequence. The fragments can range in size from four nucleotides to the entire nucleotide sequence minus one nucleotide (10 nucleotides, 20, 30, 40, 50, 100, 200, etc.).

The phrases "hybridizes", "selectively hybridizes", or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. to about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30-120 sec, an annealing phase lasting 30-120 sec, and an extension phase of about 72° C. for 1-2 min.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

Similarly, in certain embodiments, the term "isolated" when used in relation to a polypeptide, as in "an isolated polypeptide" or "an isolated antibody," refers to a polypeptide (or antibody) that is separated from at least one component or contaminant with which it is ordinarily associated in its original source. Isolated antibodies or other isolated polypeptides arethus present in a form or setting that is different from that in which they are found in nature. In certain embodiments, an isolated polypeptide (e.g., antibody) is substantially pure.

As used herein, "substantially pure" refers to material which is at least 50% pure (i.e., free from contaminants), preferably at least 90% pure, more preferably at least 95% pure, still more preferably at least 98% pure, or most preferably at least 99% pure.

"Amino acid sequence" and terms such as "polypeptide", "protein", or "peptide" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein can be produced by recombinantly or can be isolated from a naturally occurring source.

As used herein the term "portion" when in reference to a protein (as in "a portion of a given protein") refers to fragments of that protein. The fragments can range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA can be cleaved with restriction enzymes prior to electrophoresis. Following electrophoresis, the DNA can be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies can be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and can include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

By "specific binding" or "unique binding" is intended when an agent binds only to a particular ligand, receptor, or antigen. By "selective binding" is intended when an agent preferably binds to a ligand, receptor, or antigen over others by a magnitude of about two-fold or great, about five-fold or greater, about eight-fold or greater, or about ten-fold or greater.

As used herein, "about" refers to plus or minus 10% of the indicated number. For example, "about 10%" indicates a range of 9% to 11%.

Two polynucleotide or polypeptide sequences are said to be "identical" or have "identity" if the sequence of nucleotides or amino acids in the two sequences is the same when aligned for maximum correspondence as described below. Comparisons between two sequences are typically performed by comparing the sequences over a comparison window to identify and compare local regions of sequence similarity.

In some embodiments, the "percentage of identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity. In some embodiments, the comparison window may be smaller (e.g., 7 or 10 amino acids).

Optimal alignment of sequences for comparison may be conducted using the Megalign program in the Lasergene suite of bioinformatics software (DNASTAR, Inc., Madison, Wis.), using default parameters. Alternatively, the % (amino acid) identity may be obtained using one of the publicly available BLAST or BLAST-2 programs. The WU-BLAST-2 computer program (Altschul et al., Methods in Enzymology 266:460-480 (1996)). Percent (amino acid) sequence identity may also be determined using the sequence comparison program NCBI-BLAST2 (Altschul et al., Nucleic Acids Res. 25:3389-3402 (1997)). The BLAST program is based on the alignment method of Karlin and Altschul. Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997).

In certain embodiments, terms such as "treating" or "treatment" or "to treat" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus, those in need of treatment include those already with the disorder; those prone to have the disorder; those who may have had the disorder and in whom the disorder may recur; and, those in whom the disorder is to be prevented. In certain embodiments, a subject is successfully "treated" if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associate with the specific cancer; reduced morbidity and/or mortality; improvement in quality of life; a reduction in the number of or complete absence of cancer stem cells; a decrease in the proportion of cancer stem cells in a solid tumor (relative to cells in the tumor that are not cancer stem cells); inhibit the proliferation of cancer stem cells; and a delay in or an absence of relapse.

In certain embodiments, the term "therapeutically effective amount" refers to an amount of an antibody, polypeptide, polynucleotide, small organic molecule, or other drug effective to "treat" a disease or disorder in a subject. In the case of cancer, the therapeutically effective amount of the drug can, in certain embodiments, reduce the number of cancer cells; reduce the number of cancer stem cells; reduce the proportion of cancer stem cells in a solid tumor (relative to tumor cells that are not cancer stem cells); reduce the tumor size; inhibit or stop cancer cell infiltration into peripheral organs; inhibit and/or stop tumor metastasis; inhibit and stop tumor growth; relieve to some extent one or more of the symptoms associated with the cancer; inhibit the proliferation of cancer stem cells; or result in a combination of such effects on cancer cells.

The terms "inhibit" and "inhibiting" are used interchangeably herein with "disrupt" and "disrupting."

Solid Tumor Stem Cell Cancer Markers

The present invention provides markers whose expression is differentially expressed in colon cancer stem cells compared to unfractionated colon tumor cells or non-ESA+44+ colon tumor cells. Such markers find use in the diagnosis and treatment (e.g., therapeutic targeting) of various cancers, including breast and colon cancer. In certain embodiments, the solid tumor stem cell marker is LGR5.

In some embodiments, the present invention provides methods for detection of expression of stem cell cancer markers (e.g., breast cancer stem cell cancer markers). In some embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In some embodiments, the presence of a stem cell cancer marker is used to provide a prognosis to a subject. The information provided is also used to direct the course of treatment. For example, if a subject is found to have a marker indicative of a solid tumor stem cell, additional therapies (e.g., hormonal or radiation therapies) can be started at an earlier point when they are more likely to be effective (e.g., before metastasis). In addition, if a subject is found to have a tumor that is not responsive to hormonal therapy, the expense and inconvenience of such therapies can be avoided.

The present invention is not limited to the markers described above. Any suitable marker that correlates with cancer or the progression of cancer can be utilized. Additional markers are also contemplated to be within the scope of the present invention. Any suitable method can be utilized to identify and characterize cancer markers suitable for use in the methods of the present invention, including but not limited to, those described in illustrative Example 1 below. For example, in some embodiments, markers identified as being up or down-regulated in solid tumor stem cells using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with carcinogenesis and/or metastasis. Depending on the subject, panels can be analyzed alone or in combination in order to provide the best possible diagnosis and prognosis. Markers for inclusion on a panel are selected by screening for their predictive value using any suitable method, including but not limited to, those described in the illustrative examples below.

1. Detection of RNA

In some embodiments, detection of solid tumor stem cell cancer markers are detected by measuring the expression of corresponding mRNA in a tissue sample (e.g., breast cancer tissue). mRNA expression can be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of stem cell cancer markers such as LGR5 is detected by measuring the expression of the corresponding protein or polypeptide. Protein expression can be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary. antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. cDNA Microarray Technology cDNA microarrays consist of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. Full length cDNAs, expressed sequence tags (ESTs), or randomly chosen cDNAs from any library of interest can be chosen. ESTs are partially sequenced cDNAs as described, for example, in Hillier, et al., 1996, 6:807-828. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, selectively, specifically or uniquely, to cDNA obtained from mRNA derived from a single gene under the hybridization conditions of the experiment.

In a typical microarray experiment, a microarray is hybridized with differentially labeled RNA, DNA, or cDNA populations derived from two different samples. Most commonly RNA (either total RNA or poly A+ RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluorophore while cDNA derived from a second sample (representing, for example, a different cell type, tissue type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance, and various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen et al., 1998, PNAS 95:14863-14868. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself can be found, for example, in Sokal & Sneath, Principles of numerical taxonomy, xvi, 359, W. H. Freeman, San Francisco, 1963; Hartigan, Clustering algorithms, xiii, 351, Wiley, New York, 1975; Paull et al., 1989, J. Natl. Cancer Inst. 81:1088-92; Weinstein et al. 1992, Science 258:447-51; van Osdol et al., 1994, J. Natl. Cancer Inst. 86:1853-9; and Weinstein et al., 1997, Science, 275:343-9.

Further details of the experimental methods used in the present invention are found in the Examples. Additional information describing methods for fabricating and using microarrays is found in U.S. Pat. No. 5,807,522, which is herein incorporated by reference. Instructions for constructing microarray hardware (e.g., arrayers and scanners) using commercially available parts can be found at http://cmgm.stanford.edu/pbr-own/ and in Cheung et al., 1999, Nat. Genet. Supplement 21:15-19, which are herein incorporated by reference. Additional discussions of microarray technology and protocols for preparing samples and performing microarray experiments are found in, for example, DNA arrays for analysis of gene expression, Methods Enzymol, 303:179-205, 1999; Fluorescence-based expression monitoring using microarrays, Methods Enzymol, 306: 3-18, 1999; and M. Schena (ed.), DNA Microarrays: A Practical Approach, Oxford University Press, Oxford, UK, 1999. Descriptions of how to use an arrayer and the associated software are found at http://cmgm.stanford.edu/pbrown/mguide/a-rrayerHTML/ArrayerDocs.html, which is herein incorporated by reference.

4. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data, the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research use. For example, the data can be used to further optimize the inclusion or elimination of markers as useful indicators of a particular condition or stage of disease.

5. Kits

In yet other embodiments, the present invention provides kits for the detection and characterization of cancer, or for modulating the activity of a peptide expressed by one or more cancer stem cell markers such as LGR5. In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins, e.g. in a tissue sample or in a body fluid, of a solid tumor stem cell gene signature, such as the alpha-catenin signature. The kit can comprise, for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In certain embodiments the kit comprises a panel of antibodies for detecting expression of one or more of the proteins encoded by the genes of the alpha-catenin signature. In other embodiments the kit comprises pairs of primers for detecting expression of one or more of the genes of the solid tumor stem cell gene signature. In other embodiments the kit comprises a cDNA or oligonucleotide array for detecting expression of one or more of the genes of the solid tumor stem cell gene signature.

6. In vivo Imaging

In some embodiments, in vivo imaging techniques are used to visualize the expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the solid tumor stem cell cancer markers of the present invention (e.g., in breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer stem cells can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents can also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement can be achieved by effecting radiolabeling in the presence of the specific stem cell cancer marker of the present invention, to insure that the antigen binding site on the antibody will be protected.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

Therapeutic Agents

The present invention provides a variety of therapeutic agents. In certain embodiments, the agents bind at least one human LGR protein. In certain alternative embodiments, the agents bind two or more human LGR proteins. In some embodiments, the agents disrupt (partially or wholly) the binding of at least one RSPO protein (e.g., RSPO1, RSPO2, RSPO3, and/or RSPO4) to at least one LGR protein (e.g., LGR4, LGR5, and/or LGR6). In certain embodiments, the agents disrupt RSPO-activated LGR signaling, such as LGR5 signaling. In certain embodiments, the agents disrupt beta-catenin signaling.

In certain embodiments, the therapeutic agent is a biomolecule. In certain embodiments, the therapeutic agent or biomolecule is an antibody, such as an antibody that binds at least one LGR protein. Thus, the therapeutic agent or biomolecule may be an antibody that specifically binds LGR5. In certain alternative embodiments, the therapeutic agent or biomolecule is an antibody that specifically binds LGR4 or LGR6.

In certain alternative embodiments, the therapeutic agent is an antisense oligonucleotide, an siRNA molecule, or a ribozyme.

In some embodiments, the present invention provides therapies for cancer (e.g., breast cancer). In some embodiments, the therapies target cancer markers.

The present invention provides an antibody that specifically binds at least one human LGR protein. In certain embodiments, the antibody specifically binds at least one human LGR protein selected from the group consisting of LGR4, LGR5, and LGR6. In certain embodiments, the antibody specifically binds LGR5. In certain embodiments, the antibody specifically binds two or more human LGR proteins selected from the group consisting of LGR4, LGR5, and LGR6. In certain embodiments, the antibody that specifically binds at least one human LGR protein, also disrupts binding of at least one RSPO protein (e.g., RSPO1, RSPO2, RSPO3, and/or RSPO4) to the at least one human LGR protein (e.g., LGR5). In certain embodiments, the antibody that specifically binds at least one human LGR protein is characterized by an ability to disrupt RSPO activation of LGR signaling and/or an ability to disrupt beta-catenin signaling. In certain embodiments, the antibody that specifically binds at least one human LGR protein is characterized by the ability to inhibit tumor growth, such as the growth of a solid tumor comprising solid tumor stem cells. For example, in some embodiments, the antibody that specifically binds at least one human LGR protein, disrupts or inhibits RSPO binding to LGR, and inhibits tumor growth. In certain alternative embodiments, the antibody that specifically binds at least one LGR protein, also disrupts RSPO activation of LGR signaling and inhibits tumor growth. In certain alternative embodiments, the antibody that specifically binds at least one LGR protein, also disrupts RSPO activation of LGR signaling and/or beta-catenin signaling and inhibits tumor growth. (In certain embodiments, the inhibition of tumor growth provided by an antibody may, but need not necessarily be, a result of RSPO activation of LGR signaling. In certain embodiments, the inhibition of tumor growth provided by an antibody may, but need not necessarily be, a result of inhibition of the binding of an RSPO protein to an LGR protein.)

In certain embodiments, an anti-LGR antibody (or other agent) that disrupts binding of an RSPO protein to an LGR protein, disrupts at least about 25%, at least about 50%, at least about 60%, at least about 70%, at least about 80%, or at least about 90% of the binding of the RSPO protein to an LGR protein in an in vitro or in vivo assay.

Likewise, in certain embodiments, an anti-LGR antibody (or other agent) that disrupts (a) RSPO activation of LGR signaling and/or (b) beta-catenin signaling, disrupts at least about 25%, at least about 50%, at least about 60%, at least about 70%, at least about 80%, or at least about 90% of the signaling in an in vitro or in vivo assay.

In certain embodiments, the present invention provides an isolated antibody that specifically binds to an extracellular domain of a human LGR protein and inhibits growth of a solid tumor comprising solid tumor stem cells. In certain embodiments, the extracellular domain comprises amino acids 22-564 of human LGR5 (SEQ ID NO: 1). In certain embodiments, the antibody is a monoclonal antibody. In certain embodiments, the antibody is a human antibody.

In certain embodiments, the present invention provides an isolated antibody that specifically binds to an extracellular domain of a human LGR protein and disrupts RSPO activation of LGR signaling. In certain embodiments, the extracellular domain comprises amino acids 22-564 of human LGR5 (SEQ ID NO: 1). In certain embodiments, the antibody is a monoclonal antibody. In certain embodiments, the antibody is a human antibody.

The invention further provides a monoclonal anti-LGR5 antibody 88M1. The 88M1 monoclonal antibody is produced by a hybridoma cell line deposited with the American Type Culture collection (ATCC), 10801 University Blvd, Manassas, Va., 20110, USA, on Jul. 2, 2008, in accordance with the Budapest Treaty, under ATCC deposit number PTA-9342. Antibodies that specifically bind human LGR5 and (a) comprise a heavy chain variable region that has at least about 95% sequence identity (e.g., at least about 98% or about 100% sequence identity) to the heavy chain variable region of 88M1; (b) comprise a light chain variable region that has at least about 95% (e.g., at least about 98% or about 100% sequence identity) sequence identity to the light chain variable region of 88M1; (c) comprise the heavy chain CDRs of 88M1; (d) comprise the light chain CDRs of 88M1; (e) bind to an epitope capable of binding 88M1; and/or (f) compete with 88M1 in a competitive binding assay are also provided. Cells lines producing the antibodies (including, but not limited to, the hybridoma cell line having ATCC deposit number PTA-9342) and compositions comprising the antibodies are further provided. Polynucleotides encoding the light chain variable region and/or the heavy chain variable region of the monoclonal antibodies, and vectors and cells comprising the polynucleotides are also provided.

The invention further provides an antibody that binds LGR5, comprising: (a) a heavy chain CDR1 comprising SSYAIS (SEQ ID NO:35), a heavy chain CDR2 comprising GIIPIFGMANYAQKFQG (SEQ ID NO:36), and/or a heavy chain CDR3 comprising YDFITHFDF (SEQ ID NO:37); and/or (b) a light chain CDR1 comprising RASQSVSSNYLA (SEQ ID NO:32), a light chain CDR2 comprising DASNRAT (SEQ ID NO:33), and/or a light chain CDR3 comprising QQMDDFPM (SEQ ID NO:34). In some embodiments, the antibody (a) disrupts binding of a human R-spondin (RSPO) protein to LGR5; and/or (b) disrupts RSPO activation of LGR5 signaling.

The invention further provides an antibody that binds LGR5, comprising: (a) a heavy chain CDR1 comprising SNYAIG (SEQ ID NO:41), a heavy chain CDR2 comprising GIRPNFGWAKYAQKFQG (SEQ ID NO:42), and/or a heavy chain CDR3 comprising YGQGHFPSAFDY (SEQ ID NO:43); and/or (b) a light chain CDR1 comprising TGTNSDVGTYNYVH (SEQ ID NO:38), a light chain CDR2 comprising DGSNRPSG (SEQ ID NO:39), and/or a light chain CDR3 comprising QAYDSHSFNI (SEQ ID NO:40). In some embodiments, the antibody (a) disrupts binding of a human R-spondin (RSPO) protein to LGR5; and/or (b) disrupts RSPO activation of LGR5 signaling.

The invention further provides an antibody that binds LGR5, comprising: (a) a heavy chain variable region having at least about 80% sequence identity to SEQ ID NO:45; and/or (b) a light chain variable region having at least about 80% sequence identity to SEQ ID NO:44. In certain embodiments, the antibody comprises a heavy chain variable region having at least about 85%, at least about 90%, at least about 95%, at least about 98%, or 100% sequence identity to SEQ ID NO:45. In certain embodiments, the antibody comprises a light chain variable region having at least about 85%, at least about 90%, at least about 95%, at least about 98%, or 100% sequence identity to SEQ ID NO:44. In certain embodiments, the antibody (a) disrupts binding of a human R-spondin (RSPO) protein to LGR5; and/or (b) disrupts RSPO activation of LGR5 signaling. Polynucleotides comprising a polynucleotide encoding such heavy chain or light chain variable regions are also provided.

In certain embodiments, the antibody comprises the heavy chain variable region of SEQ ID NO: 45 and the light chain variable region of SEQ ID NO: 44. The invention also provides antibodies that compete for binding to LGR5 with such an antibody in a competitive binding assay.

The invention further provides an antibody that binds LGR5, comprising: (a) a heavy chain variable region having at least about 80% sequence identity to SEQ ID NO:47; and/or (b) a light chain variable region having at least about 80% sequence identity to SEQ ID NO:46. In certain embodiments, the antibody comprises a heavy chain variable region having at least about 85%, at least about 90%, at least about 95%, at least about 98%, or 100% sequence identity to SEQ ID NO:47. In certain embodiments, the antibody comprises a light chain variable region having at least about 85%, at least about 90%, at least about 95%, at least about 98%, or 100% sequence identity to SEQ ID NO:46. In certain embodiments, the antibody (a) disrupts binding of a human R-spondin (RSPO) protein to LGR5; and/or (b) disrupts RSPO activation of LGR5 signaling. Polynucleotides comprising a polynucleotide encoding such heavy chain or light chain variable regions are also provided.

In certain embodiments, the antibody comprises the heavy chain variable region of SEQ ID NO: 47 and the light chain variable region of SEQ ID NO: 46. The invention also provides antibodies that compete for binding to LGR5 with such an antibody in a competitive binding assay.

Competition assays can be used to determine whether two antibodies bind the same epitope by recognizing identical or sterically overlapping epitopes. Any method known in the art for determining competitive binding (such as e.g., the immunoassays described elsewhere herein) may be used.

In vitro and in vivo assays for screening candidate therapeutic agents that have the ability to specifically bind a particular LGR protein are well known in the art. Immunoassays which can be used for assessing binding by antibodies include, for example, competitive and noncompetitive assays systems using techniques such as Western blots, radioimmunoassay, ELISA (enzyme-linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. The use of FACS analysis to determine specific binding to a target LGR protein is outlined in the specific example, Example 3 below.

In addition, the binding affinity of an antibody to an LGR protein and the off-rate of the antibody to LGR interaction can be determined by competitive binding assays. One example of a competitive binding assay is a radioimmunoassay comprising the incubation of labeled LGR or RSPO protein with the antibody of interest in the presence of increasing amounts of unlabeled LGR or RSPO protein, and the detection of the antibody bound to the labeled LGR protein. The affinity of the antibody for the LGR protein and the binding off-rates can then be determined from the data by Scatchard plot analysis. Competition with a second antibody (e.g., 88M1) can also be determined using radioimmunoassays. For example, the LGR or RSPO protein is incubated with the antibody of interest conjugated to a labeled compound in the presence of increasing amounts of an unlabeled second antibody. Alternatively, the binding affinity of an antibody to an LGR or RSPO protein and the on- and off-rates of an antibody-LGR interaction can be determined by surface plasmon resonance, such as BIAcore. In certain embodiments, the anti-LGR antibodies can be targeted to and accumulate on the membrane of an LGR-expressing cell.

Additional assays known in the art for assessing the binding or other interaction of a candidate therapeutic agent (including those which are not antibodies) with a protein such as an LGR are described below in the section entitled "Drug screening."

Assays suitable for determining whether a candidate therapeutic agent (such as an anti-LGR antibody) is capable of blocking binding of an RSPO protein to an LGR protein are likewise well known in the art. Examples of such competitive binding assays are described elsewhere herein. An example of the use of a FACS-based competitive binding assay to determine the ability of an antibody to LGR5 to at least partially block binding of RSPO1 to LGR5 is provided in the specific example, Example 3, below.

In addition, assays for determining whether a particular candidate therapeutic agent is capable of disrupting RSPO activation of LGR signaling (e.g., LGR5 signaling) and/or is capable of disrupting beta-catenin signaling are also known in the art. For examples assays employing the use of reporter genes operably linked to a beta-catenin responsive promoter may be used to measure the level of beta-catenin signaling in the presence of an anti-LGR antibody. See, e.g., the luciferase assays described in the specific example Example 2 below.

In vitro and in vivo assays for screening candidate therapeutic agents that target an LGR protein for anti-tumor and/or anti-cancer stem cell efficacy will be apparent to one skilled in the art. Exemplary assays known in the art are provided below in the section entitled "Drug Screening" and in the specific example, Example 4, below. In addition further guidance regarding assessing anti-tumor and anti-cancer stem cell efficacy are provided in International Patent Publication No. WO 08/042,236, U.S. Patent Publication No. US 2007/0117751, and U.S. Patent Publication Nos. US 2008/0131434, each of which is hereby incorporated by reference herein in its entirety.

Antibodies (Including Antibody Fragments)

As described above, in certain embodiments, the therapeutic agents are antibodies, such as antibodies to a human LGR protein. In addition, the present invention provides antibodies useful for other purposes, such as for diagnostic or screening purposes. In certain embodiments, the antibodies described herein (including, but not limited to, therapeutic antibodies) are isolated. In certain embodiments, the antibodies described herein are substantially pure.

In some embodiments the antibodies (whether for use in therapy or other purposes) are monoclonal antibodies. In certain embodiments, the antibodies are chimeric, humanized, or human antibodies. The invention further provides bispecific antibodies. In certain embodiments, the antibodies are antibody fragments, such as Fab fragments.

In certain embodiments, the present invention provides isolated antibodies against a cancer stem cell marker (e.g., LGR5). The antibody, or antibody fragment, can be any monoclonal or polyclonal antibody that specifically recognizes the described colon cancer stem cell marker. In some embodiments, the present invention provides monoclonal antibodies, or fragments thereof, that specifically bind to a colon cancer stem cell marker polypeptide described herein. In some embodiments, the monoclonal antibodies, or fragments thereof, are chimeric or humanized antibodies that specifically bind to the extracellular domain of a colon cancer stem cell marker polypeptide described herein. In other embodiments, the monoclonal antibodies, or fragments thereof, are human antibodies that specifically bind to the extracellular domain of a colon cancer stem cell marker polypeptide described herein.

The antibodies against a cancer stem cell marker find use in the experimental, diagnostic and therapeutic methods described herein. In certain embodiments, the antibodies of the present invention are used to detect the expression of a colon cancer stem cell marker protein in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a colon cancer stem cell marker, for example, on tumor cells, in cell lysates, or in other protein samples. In other embodiments, the antibodies of the present invention are used to inhibit the growth of tumor cells by contacting the antibodies with tumor cells either in vitro cell based assays or in vivo animal models. In still other embodiments, the antibodies are used to treat cancer in a human patient by administering a therapeutically effective amount of an antibody against a colon cancer stem cell marker.

Polyclonal antibodies can be prepared by any known method. Polyclonal antibodies can be raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against a colon cancer stem cell marker is a humanized antibody. Humanized antibodies are antibodies that contain minimal sequences from non-human (e.g. murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a colon cancer stem cell marker. Bispecific antibodies are antibodies that are capable of specifically recognizing and binding at least two different epitopes. The different epitopes can either be within the same molecule (e.g. the same colon cancer stem cell marker polypeptide) or on different molecules such that both, for example, the antibodies can specifically recognize and bind a colon cancer stem cell marker as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from $E.$ $coli$ or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, $Aleurites$ $fordii$ proteins, dianthin proteins, $Phytolaca$ $americana$ proteins (PAPI, PAPII, and PAP-S), $momordica$ $charantia$ inhibitor, curcin, crotin, $sapaonaria$ $officinalis$ inhibitor, gelonin, mitogellin, restrictocin, phenomycin, enomycin, and the tricothecenes. A variety of radionuclides are available for the production of radioconjugated antibodies including $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

In some embodiments the antibody of the invention contains human Fc regions that are modified to enhance effector function, for example, antigen-dependent cell-mediated cytotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, J. Exp Med. 176:1191-1195; Shopes, 1992, Immunol. 148:2918-2922). Homodimeric antibodies with enhanced anti-tumor activity can also be prepared using heterobifunctional cross-linkers as described in Wolff et al., 1993, Cancer Research 53:2560-2565. Alternatively, an antibody can be engineered which has dual Fc regions (Stevenson et al., 1989, Anti-Cancer Drug Design 3:219-230).

In some embodiments, the present invention provides antibodies that target tumors that express a stem cell cancer marker of the present invention. Any suitable antibody (e.g., monoclonal, polyclonal, or synthetic) can be utilized in the therapeutic methods disclosed herein. In some embodiments, the antibodies used for cancer therapy are humanized antibodies. Methods for humanizing antibodies are well known in the art (See e.g., U.S. Pat. Nos. 6,180,370, 5,585,089, 6,054, 297, and 5,565,332; each of which is herein incorporated by reference).

In some embodiments, the therapeutic antibodies comprise an antibody generated against a stem cell cancer marker of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention can include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments can include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some embodiments, deglycosylated ricin A chain is utilized.

In any event, it is proposed that agents such as these can, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a stem cell cancer marker of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In some embodiments, antibody based therapeutics are formulated as pharmaceutical compositions as described below. In some embodiments, administration of an antibody composition of the present invention results in a measurable decrease in cancer (e.g., decrease or elimination of tumor).

The invention further provides kits and articles of manufacture comprising one or more antibodies. In certain embodiments, the kits comprise at least two antibodies. In certain embodiments, the kits comprise at least two antibodies that specifically bind a human LGR protein.

Drug Screening

In some embodiments, the present invention provides drug screening assays (e.g., to screen for anticancer drugs). In certain embodiments, the screening methods of the present invention utilize stem cell cancer markers identified using the methods of the present invention. For example, in some embodiments, the present invention provides methods of screening for compound that alter (e.g., increase or decrease) the expression of stem cell cancer marker genes. In some embodiments, candidate compounds are antisense agents or siRNA agents (e.g., oligonucleotides) directed against cancer markers. In other embodiments, candidate compounds are antibodies that specifically bind to a stem cell cancer marker of the present invention. In certain embodiments, libraries of compounds of small molecules are screened using the methods described herein.

In one screening method, candidate compounds are evaluated for their ability to alter stem cell cancer marker expression by contacting a compound with a cell expressing a stem cell cancer marker and then assaying for the effect of the candidate compounds on expression. In some embodiments, the effect of candidate compounds on expression of a cancer marker gene is assayed by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein. In some embodiments, other changes in cell biology (e.g., apoptosis) are detected.

Specifically, the present invention provides screening methods for identifying modulators, i.e., candidate or test compounds or agents (e.g., proteins, peptides, peptidomimetics, peptoids, small molecules or other drugs) which bind to, or alter the signaling or function associated with the cancer markers of the present invention, have an inhibitory (or stimulatory) effect on, for example, stem cell cancer marker expression or cancer markers activity, or have a stimulatory or inhibitory effect on, for example, the expression or activity of a cancer marker substrate. Compounds thus identified can be used to modulate the activity of target gene products (e.g., stem cell cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic cancer or eliminating or controlling tumor stem cells to prevent or reduce the risk of cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Natl. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a stem cell cancer marker protein or biologically active portion thereof is contacted with a test compound, and the ability of the test compound to modulate the cancer marker's activity is determined. Determining the ability of the test compound to modulate stem cell cancer marker activity can be accomplished by monitoring, for example, changes in enzymatic activity. The cell, for example, can be of mammalian origin.

The ability of the test compound to modulate cancer marker binding to a compound, e.g., a stem cell cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the stem cell cancer marker is coupled with a radioisotope or enzymatic label to monitor the ability of a test compound to modulate cancer marker binding to a cancer markers substrate in a complex. For example, compounds (e.g., substrates) can be labeled with $^{125}$I, $^{35}$S $^{14}$C or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a stem cell cancer marker substrate) to interact with a stem cell cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the stem cell cancer marker protein or biologically active portion thereof is evaluated. Biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FRET binding event can be conveniently measured through standard fluorometric detection means well known in the art (e.g., using a fluorimeter).

In another embodiment, determining the ability of the stem cell cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. The target gene product can be anchored onto a solid surface, and the test compound, (which is not anchored), can be labeled, either directly or indirectly, with detectable labels discussed herein.

It may be desirable to immobilize stem cell cancer markers, an anti-cancer marker antibody or its target molecule to facilitate separation of complexed from non-complexed forms of one or both of the proteins, as well as to accommodate automation of the assay. Binding of a test compound to a stem cell cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with stem cell cancer marker protein or target molecules but which do not interfere with binding of the stem cell cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known (See e.g., Heegaard J. Mol. Recognit. 11:141-8 [1998]; Hageand Tweed J. Chromatogr. Biomed. Sci. Appl 699:499-525 [1997]). Further, fluorescence energy transfer can also be conveniently utilized, as described herein, to detect binding without further purification of the complex from solution.

The assay can include contacting the stem cell cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that stem cell cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of stem cell cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein (e.g. to treat a human patient who has cancer).

In certain embodiments, the present invention provides methods for screening candidate drugs, including, but not limited to, antibodies, for their ability to (a) specifically bind a human LGR protein; (b) disrupt binding between a human RSPO protein and a human LGR protein and/or (c) disrupt RSPO activation of LGR signaling.

Pharmaceutical Compositions and Methods

The present invention further provides pharmaceutical compositions (e.g., comprising a small molecule, antisense, antibody, or siRNA that, for example, targets the stem cell cancer markers of the present invention). Thus, pharmaceutical compositions comprising one or more of the therapeutic agents described herein, such as the antibodies targeting LGR proteins, are provided. In certain embodiments, the pharmaceutical compositions comprising the one or more therapeutic agents described herein further comprise a pharmaceutically acceptable carrier.

The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level can also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The present invention provides pharmaceutical composition comprising (a) one or more of the therapeutic agents described herein and (b) a second anticancer agent. In certain embodiments, the second anticancer agent is a chemotherapeutic agent. Certain embodiments of the invention provide pharmaceutical compositions containing (a) one or more compounds that modulate the activity of a stem cell cancer marker (e.g. antibody, small molecule, siRNA, anti-sense, etc.) and (b) one or more other chemotherapeutic agents.

Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). In certain embodiments, the chemotherapeutic agent is irinotecan or paclitaxel. Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. Other chemotherapeutic agents are also within the scope of this invention.

Two or more combined compounds can be used together or sequentially.

Dosing is dependent on severity and responsiveness of the disease state to be treated, with the course of treatment lasting from several days to several months, or until a cure is effected or a diminution of the disease state is achieved (e.g. reduction in tumor size). Optimal dosing schedules can be calculated from measurements of drug accumulation in the body of the patient. The administering physician can easily determine optimum dosages, dosing methodologies and repetition rates. Optimum dosages can vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and can be given once or more daily, weekly, monthly or yearly. The treating physician can estimate repetition rates for dosing based on measured residence times and concentrations of the drug in bodily fluids or tissues. Following successful treatment, it can be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

The invention provides methods of treating cancer comprising administering one or more of the therapeutic agents described herein to a subject (e.g., human). In certain embodiments, the cancer involves cancer stem cells. In certain embodiments, the cancer treated is breast cancer or colon cancer.

In some embodiments, the subject treated by the methods described herein has a solid tumor. In some embodiments, the subject treated by the methods described herein has had a solid tumor removed. In certain embodiments, the tumor comprises solid tumor stem cells. In certain embodiments, the tumor is a tumor that overexpresses LGR5 (relative to normal cells of the same tissue type). In certain embodiments, the tumor does not significantly overexpress a Wnt protein relative to normal tissue, and the tumor therefore exhibits normal Wnt expression. In some alternative embodiments, the tumor overexpresses at least one Wnt protein.

In certain embodiments, a subject having a tumor is screened to identify whether the tumor overexpresses LGR5 or comprises cancer stem cells overexpressing LGR5 prior to administration of the therapeutic agent.

The invention provides methods of treating cancer and/or inhibiting growth of a tumor in a human, comprising administering to the human a therapeutically effective amount of one or more therapeutic agents or biomolecules described herein. In certain embodiments, the cancer or tumor comprises cancer stem cells.

The invention provides a method of treating cancer or inhibiting growth of a tumor in a human, comprising administering to the human a therapeutically effective amount of an agent that (a) disrupts the binding of a human R-spondin (RSPO) protein to a human leucine-rich repeat-containing G protein-coupled receptor (LGR); and/or (b) disrupts RSPO activation of LGR signaling.

The invention further provides a method of treating cancer or inhibiting tumor growth by inhibiting beta-catenin signaling in a tumor cell, comprising contacting said tumor cell with an agent that (a) disrupts the binding of a human R-spondin (RSPO) protein to a human leucine-rich repeat-containing G protein-coupled receptor (LGR); and/or (b) disrupts RSPO activation of LGR signaling. In certain embodiments, the method is an in vivo method. In alternative embodiments, the method is an in vitro method.

In certain embodiments, the present invention provides a method of treating cancer comprising cancer stem cells, the method comprising administering a therapeutically effective amount of an antibody that specifically binds to an extracellular domain of a human LGR protein. In certain embodiments, the extracellular domain comprises amino acids 22-564 of human LGR5 (SEQ ID NO: 1). In certain embodiments, the antibody is a monoclonal antibody. In certain embodiments, the antibody is a human antibody.

In certain embodiments, the present invention provides a method of inhibiting tumor growth, the method comprising administering a therapeutically effective amount of an antibody that specifically binds to a human LGR protein. In certain embodiments, the human LGR protein is LGR5. In certain embodiments, the antibody is a monoclonal antibody. In certain embodiments, the antibody is a human antibody. In certain embodiments, the tumor is a tumor comprising solid tumor stem cells. In certain embodiments, the antibody disrupts binding of a human RSPO protein to the human LGR protein. In certain alternative embodiments, the antibody disrupts RSPO activation of LGR signaling and/or disrupts beta-catenin signaling.

The invention further provides methods of inhibiting the proliferation of cancer stem cells and/or decreasing the number or proportion of cancer stem cells in a subject comprising administering to the subject one or more of the therapeutic agents described herein, including, but not limited to anti-LGR antibodies.

In certain embodiments, the methods comprising administration of a therapeutic agent to a subject further comprise administration of a second anticancer agent to the subject. The therapeutic agent and second anticancer agent may be administered at the same time (concurrently) or at different times (e.g., sequentially). In certain embodiments, the two agents are administered to the subject as part of the same composition. In certain embodiments, the therapeutic agent is administered to the subject in one composition, whereas the second anticancer agent is administered to the subject in a second composition.

In certain embodiments, the subjects are mammals. In certain embodiments, the subjects to which the therapeutic agents are administered are humans.

The present invention further provides kits and articles of manufacture comprising both a therapeutic agent described herein, as well as a second anticancer agent. In certain embodiments the second anticancer agent is a chemotherapeutic agent.

Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms) or knock-outs thereof. In some embodiments, the transgenic animal displays an altered phenotype (e.g., increased or decreased presence of markers) as compared to wild-type animals. Methods for analyzing the presence or absence of such phenotypes include but are not limited to, those disclosed herein. In some embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., 1985, PNAS 82:44384442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, 1976, PNAS 73:1260). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., 1985, PNAS 82:6927). Transfection is easily and efficiently obtained by culturing the blastomeres on a monolayer of virus-producing cells (Stewart, et al., 1987, EMBO J., 6:383).

Alternatively, infection can be performed at a later stage. Virus or virus-producing cells can be injected into the blastocoele (Jahner et al., 1982, Nature 298:623). Most of the founders will be mosaic for the transgene since incorporation occurs only in a subset of cells that form the transgenic animal. Further, the founder can contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, 1995, Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al., 1981, Nature 292:154; Bradley et al., 1984, Nature 309:255; Gossler et al., 1986, PNAS 83:9065; and Robertson et al., 1986, Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science, 1988, 240:1468). Prior to the introduction of transfected ES cells into the blastocoel, the transfected ES cells can be subjected to various selection protocols to enrich for ES cells which have integrated the transgene assuming that the transgene provides a means for such selection. Alternatively, the polymerase chain reaction can be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain embodiments and aspects of the present invention and are not to be construed as limiting the scope thereof.

Example 1

LGR5 is Over-Expressed in Cancer Stem Cells Relative to Non-Tumorigenic Tumor Cells Recently it has been demonstrated that malignant human breast tumors harbor a small, distinct population of cancer stem cells that are enriched for the ability to form tumors in immunodeficient mice. An ESA+, CD44+, CD24−/low, Lin− cell population was found to be 50-fold enriched for tumorigenic breast tumor cells compared to unfractionated tumor cells (Al-Hajj et al., 2003, PNAS 100:3983-8). A similar population of ESA+CD44+ cancer stem cells has been identified in colon cancers (U.S. patent application Ser. No. 11/591,019). Microarray analysis of FACS sorted tumorigenic cancer stem cells compared to non-tumorigenic tumor cells has revealed a number of cancer stem cell markers upregulated in cancer stem cells relative to non-tumorigenic tumor cells. (U.S. patent application Ser. Nos. 10/864,207 and 11/050,282).

These microarray data also revealed that LGR5 is overexpressed in colon cancer stem cells compared to non-tumorigenic tumor cells (FIG. 1). Tumorigenic (TG) colon cancer stem cells were isolated from bulk tumor cells based on cell surface markers using FACS. Specifically, cells were counted, washed twice with HBSS containing 2% heat-inactivated calf serum (HICS) and 25 mM HEPES, and resuspended at $10^6$ cells per 100 ul. Tumor cells were incubated with rat anti-mouse CD3, CD4, CD8, Ter119, Mac1 and Gr1 antibodies conjugated to a magnetic bead and run over a magnetic column to remove mouse hematopoietic cells.

Tumors cells were then incubated with a sheep anti-rat antibody conjugated to Cy5.5-PE and the viability dye propidium iodide to detect and remove the remaining mouse hematopoietic and dead cells, respectively. After blocking, the cells were further incubated with fluorescently conjugated antibodies against mouse H-2K$^d$ cells, human ESA (Miltenyi Biotec; Auburn, Calif.) and CD44, (Bioscience, San Diego, Calif.) to remove mouse cells and to positively select human tumor cells expressing ESA and CD44. Flow cytometry was performed on a FACSAria (Becton Dickinson, Franklin Lakes, N.J.) with the use of side scatter and forward scatter profiles to select for single cells. Cy5.5-PE+ and propidium iodide positive cells were first excluded and a fraction of ESA+44+ cells was isolated independently of a fraction of non-ESA+ 44+ tumor cells.

Microarray analysis was utilized to identify markers for colon cancer stem cells versus non-tumorigenic tumor cells. Total RNA from FACS sorted tumorigenic cancer stem cells and non-tumorigenic solid tumor cells was isolated using RNasy (Qiagen, Valencia, Calif.) according to the manufacturer's protocol. Probes for microarray analysis were prepared and hybridized to Affymetrix HG-U133 gene chips according to Affymetrix protocols (Affymetrix, Santa Clara, Calif.). Arrays were scanned with an argon-ion laser confocal microscope and the intensity for each probe set on the array was assessed with Affymetrix Microarray Suite 4.0 software according to Affymetrix procedures. Microarray analysis of three different colon cancers (C4, C6, and C9) revealed the over-expression of LGR5 in tumorigenic solid tumor stem cells compared to non-tumorigenic solid tumor cells (FIG. 1).

Figure 2:
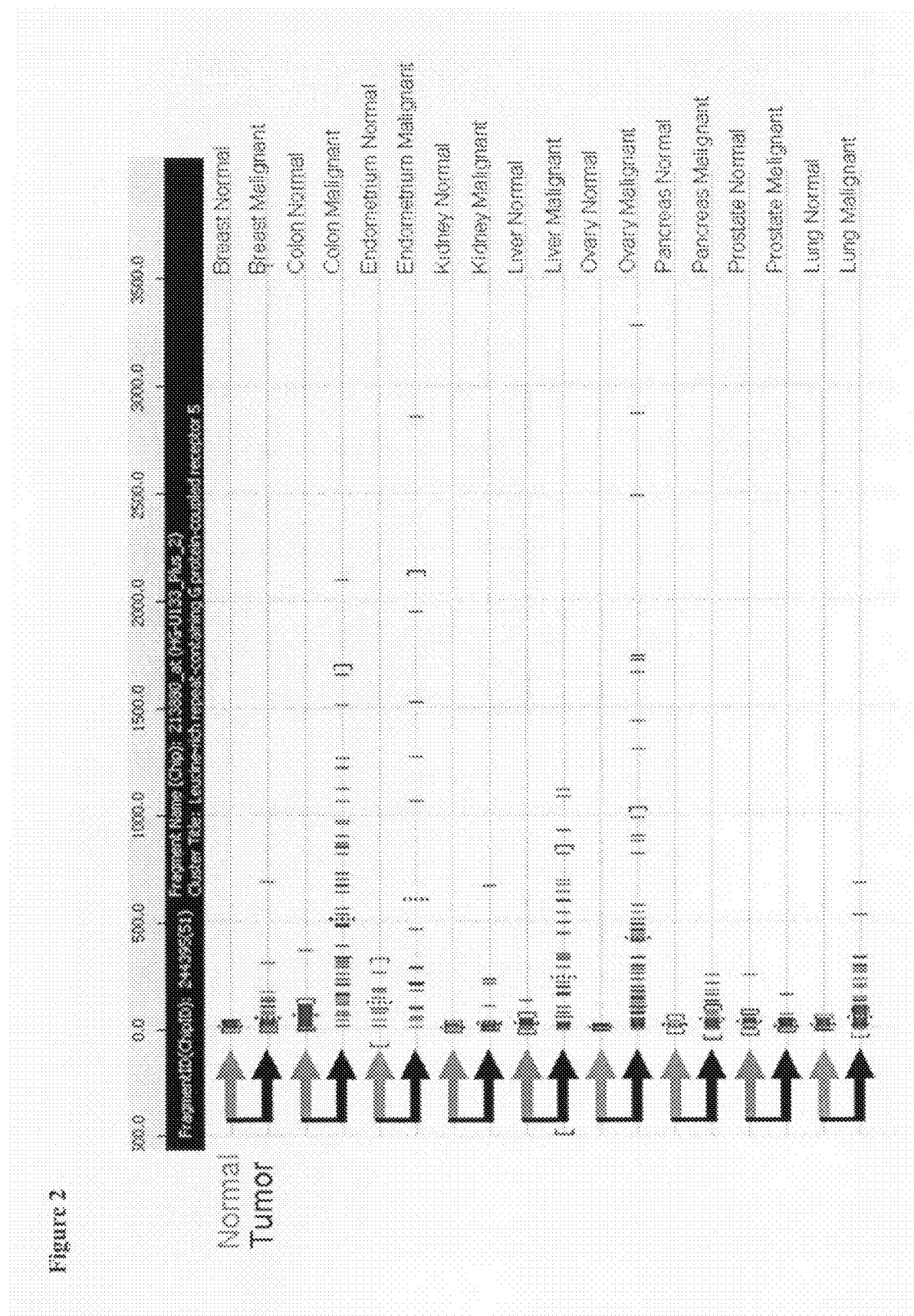
FIG. 2. LGR5 Is Overexpressed In Human Epithelial Tumors. Shown is microarray data for LGR5 mRNA expression from a large number of human tumors compared to tissue samples from normal human tissues. Expression level of LGR5 in individual patient samples is indicated by vertical dash lines within the horizontal axis for each indicated tissue type. LGR5 is overexpressed in most tumor samples relative to the expression in the corresponding normal tissue.
Figure 3:
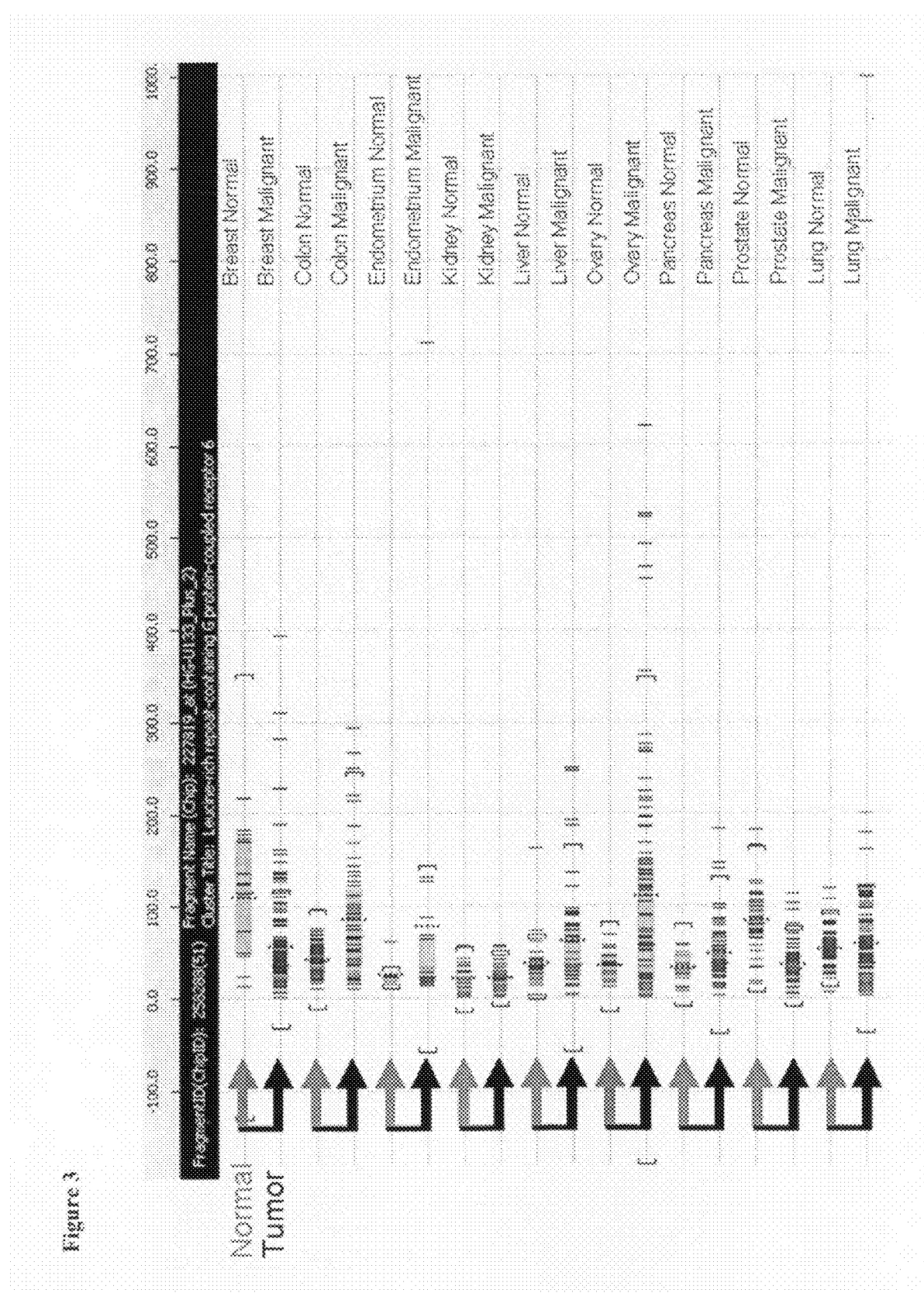
FIG. 3. LGR6 Shows Altered Expression In Human Epithelial Tumors. Shown is microarray data for LGR6 mRNA expression from a large number of human tumors compared to tissue samples from normal human tissues. Expression level of LGR6 in individual patient samples is indicated by vertical dash lines within the horizontal axis for each indicated tissue type. LGR6 expression shows altered expression in many tumor samples relative to the expression in the corresponding normal tissue.

Microarray analysis using mRNA isolated from tumors and corresponding normal tissue from a large number of human patients (GeneLogic BioExpress Datasuite) further revealed increased expression of LGR5 as well as LGR6 in human tumors of epithelial origin. Expression of LGR5 in individual patient samples from a wide range of epithelial tumors was compared to expression in normal organ epithelia. LGR5 on chip HG-U133_Plus_2, fragmentID(ChipID) 244395(51), showed increased expression in most tumors but especially in colon, liver, ovary, and lung tumors (FIG. 2). Similarly, LGR6 on chip HG-U133_Plus_2, fragmentID (ChipID) 258288(51), showed altered expression in most epithelial tumors (FIG. 3).

Example 2

RSPO1 Activates Beta-Catenin Signaling Via LGR5

This example describes the activation of beta-catenin signaling by RSPO1 via LGR5.

Figure 4:
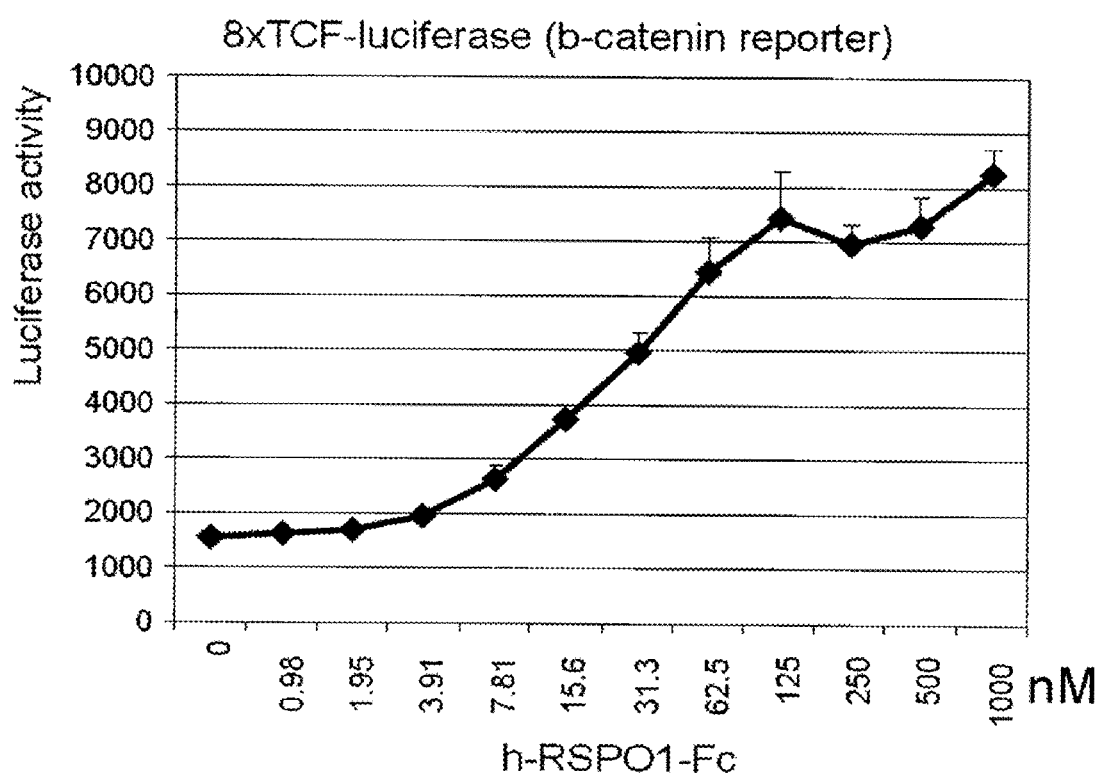
FIG. 4. RSPO1 Activates Beta-Catenin Signaling. Luciferase activity (y-axis) from an 8×TCF luciferase reporter was measured following exposure to RSPO1-Fc in the indicated concentration x-axis). RSPO1-Fc induced luciferase activity from the beta-catenin responsive promoter in a dose dependent manner.

In certain embodiments, an 8×TCF luciferase reporter assay demonstrated RSPO1 activates expression of a beta-catenin responsive promoter. A RSPO1-Fc construct was generated using standard recombinant DNA techniques. Specifically, full-length, human RSPO1 was ligated in-frame to human Fc and the recombinant RSPO1-Fc protein expressed in insect cells using baculovirus. Recombinant RSPO1-Fc was then purified from the conditioned insect medium using protein A chromatography. HEK 293 cells stably transfected with an 8×TCF luciferase reporter were exposed to RSPO1-Fc at increasingly higher concentrations for a total of twelve hours. Reporter cells showed greater luciferase activity in response to increasing concentrations of RSPO1 (FIG. 4).

Figure 5:
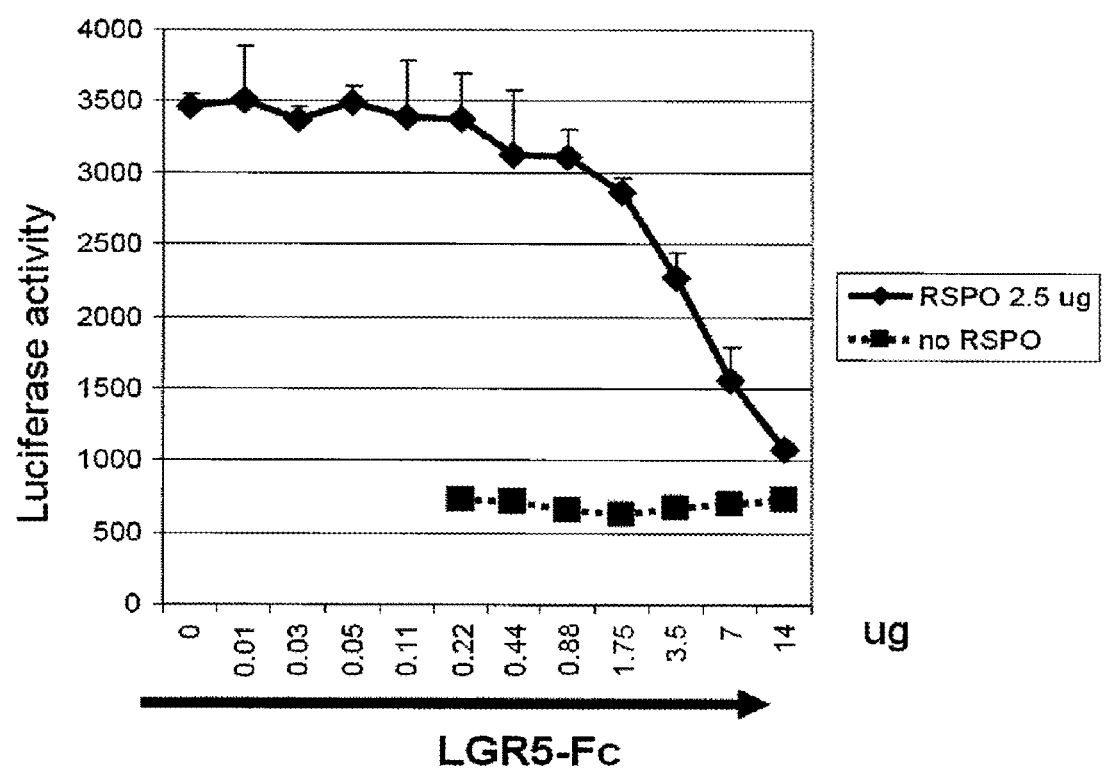
FIG. 5. Soluble LGR5 (LGR5-Fc) Inhibits the Induction of Beta-Catenin Signaling By RSPO1. Luciferase activity (y-axis) from cells transfected with an 8×TCF luciferase reporter was measured in response to exposure to control medium (squares, no RSPO) or RSPO1-Fc in combination with increasing concentrations of soluble LGR5 (diamonds, RSPO 2.5 ug).

The effect of soluble LGR5 on RSPO1 activation of the 8×TCF beta-catenin responsive promoter was assessed (FIG. 5). A soluble LGR5-Fc construct was generated using standard recombinant DNA techniques. Specifically, amino acids 1 to 564 of human LGR5 were ligated in frame to human Fc and the recombinant LGR5-Fc was expressed in insect cells using baculovirus. Cleavage of the LGR5 signal sequence results in a mature LGR5-Fc fusion protein containing amino acids 22-564 of LGR5. HEK 293 cells stably transfected with an 8×TCF luciferase reporter construct were cultured in 96 well plates and exposed to either: control medium; 2.5 ug RSPO1-Fc; or RSPO1-Fc in combination with increasing concentrations of soluble LGR5-Fc for 24 hours. Soluble LGR5 inhibited RSPO1 activation of luciferase activity via the beta-catenin responsive promoter.

Figure 6A:
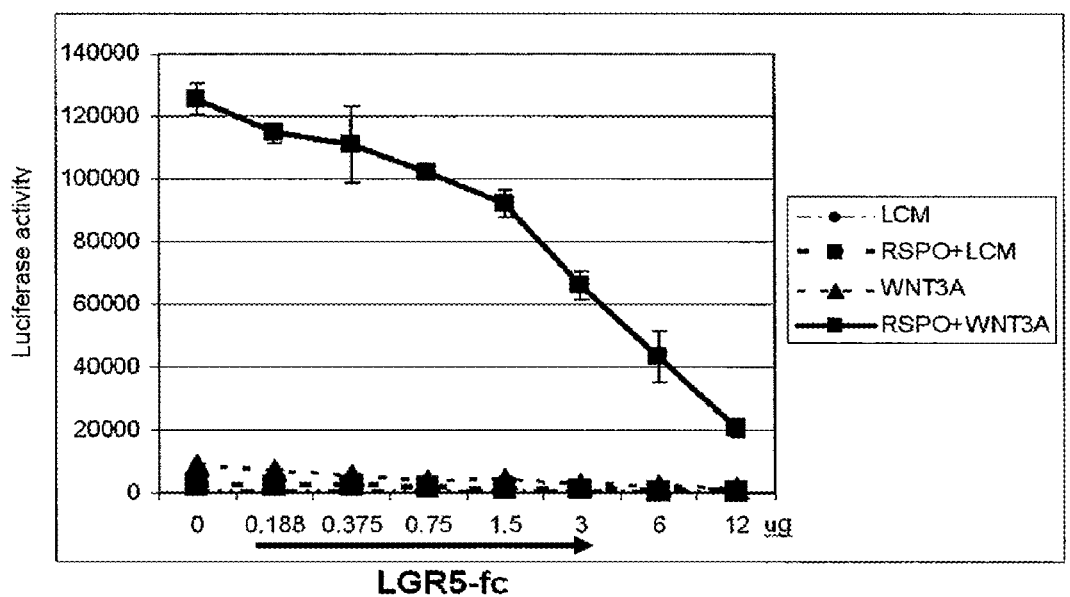
FIG. 6. Soluble LGR5, but not Soluble FZD10, Inhibits the Synergistic Induction of Beta-Catenin Signaling by RSPO1 and Wnt3A. A) Soluble LGR5 inhibits the synergistic induction of beta-catenin signaling by RSPO1 and Wnt3A. Luciferase activity (y-axis) from cells transfected with an 8×TCF luciferase reporter was measured in response to exposure to control medium (diamonds, LCM); RSPO1 and LCM (squares, RSPO+LCM); Wnt3A (triangles); and RSPO1 plus Wnt3A (crosses). Increasing concentrations of soluble LGR5 (x-axis) reduced the synergistic induction of luciferase activity by RSPO1 and Wnt3A. B) Soluble FZD10 does not inhibit the synergistic induction of beta-catenin signaling by RSPO1 and Wnt3A. Luciferase activity (y-axis) from cells transfected with an 8×TCF luciferase reporter was measured in response to exposure to control medium (diamonds, LCM); RSPO1 and LCM (squares, RSPO+LCM); Wnt3A (triangles); and RSPO1 plus Wnt3A (crosses). Increasing concentrations of soluble LGR5 (x-axis) reduced the synergistic induction of luciferase activity by RSPO1 and Wnt3A.
Figure 6B:
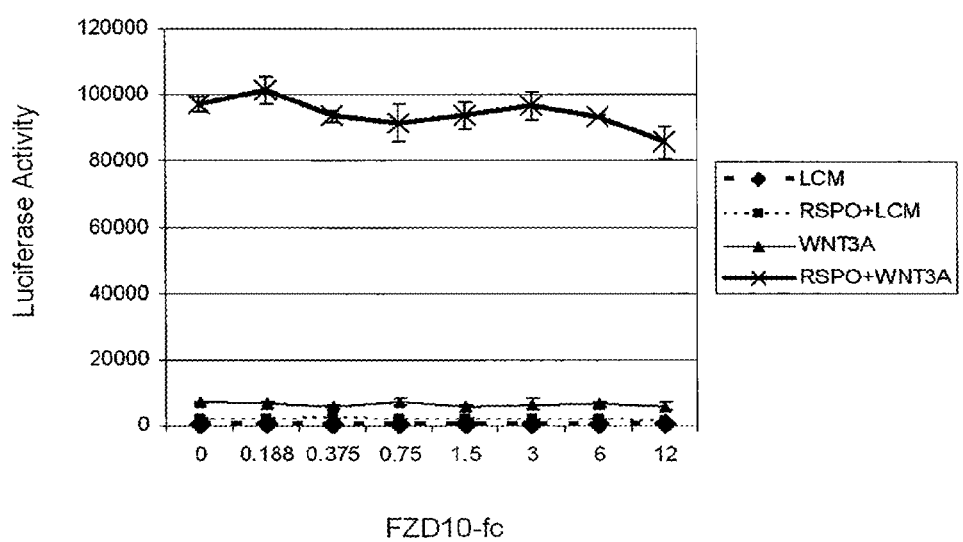

Soluble LGR5 also specifically inhibits the synergistic activation of beta-catenin signaling by RSPO1 and Wnt3B. HEK 293 cells stably transfected with an 8×TCF luciferase reporter construct were cultured in 96 well plates and exposed to either: control medium (LCM, L cell conditioned medium); 2.5 ug RSPO1-Fc in LCM; Wnt3A (Wnt 3A containing L cell conditioned medium); or a combination of RSPO1-Fc and Wnt3A along with increasing concentrations of soluble LGR5-Fc (FIG. 6A) or soluble FZD10-Fc (FIG. 6B) for 24 hours. RSPO1 and Wnt3A act synergistically in activating luciferase activity from the beta-catenin promoter, and soluble LGR5 inhibited this activation (FIG. 6A). In contrast, soluble FZD10 had no effect (FIG. 6B).

Figure 7A:
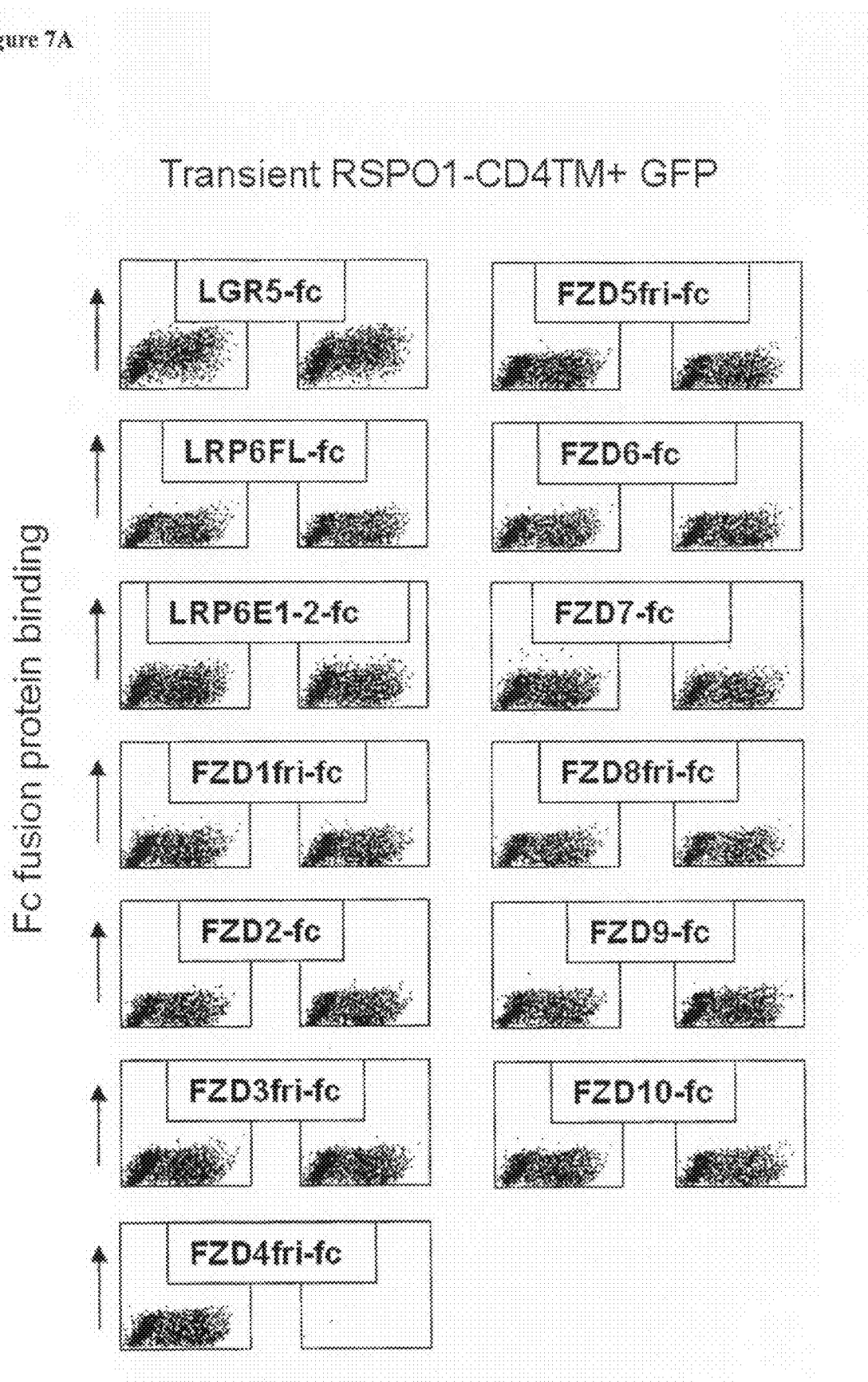
FIG. 7. RSPO1 Activates Beta-Catenin Signaling via Binding to LGR5. A) HEK 293 cells transiently transfected with RSPO1-CD4TM and GFP were incubated with LGR5-Fc, LRP6FL-Fc, LRP6E1-2-Fc, or FZD1-10-Fc as indicated. FACS based on GFP (x-axis) and Fc fusion protein binding (y-axis) demonstrated binding between RSPO1 and LGR5 (top left). RSPO1 only weakly bound LRP6 and failed to interact with any FZD. B) HEK 293 cells transiently transfected with FLAG-LGR5-CD4TM and GFP were incubated in the presence of heparin with (in duplicate) RSPO1-Fc (top), FZD8-Fc (middle), or a FLAG antibody as a positive control (bottom). FACS based on GFP (x-axis) and Fc fusion protein binding (y-axis) demonstrated binding between RSPO1 and LGR5 but not FZD8.C) All RSPO family members are able to bind to LGR5. HEK 293 cells transiently transfected with FLAG-LGR5-CD4TM and GFP were incubated in the presence of heparin with RSPO1-Fc, RSPO2-Fc, RSPO3-Fc, RSPO4-Fc, FZD8-Fc, or a FLAG antibody as a positive control as indicated. FACS based on GFP (x-axis) and Fc fusion protein binding (y-axis) demonstrated binding between each RSPO family member and LGR5 as indicated by FACS signal within the upper right hand boxed quadrant of each FACS plot.

To determine the mechanism by which RSPO1 activates beta-catenin signaling, FACS analysis was used to assess binding between RSPO1 and LGR5. In certain embodiments, binding between soluble LGR5 and cell-surface RSPO1 was determined. A cell-surface RSPO1 protein was generated by ligating full-length human RSPO1 to the transmembrane domain of CD4 using standard recombinant DNA techniques (RSPO1-CD4TM). HEK 293 cells were transiently transfected RSPO1-CD4TM and GFP. After 48 hours, cells were suspended in ice cold PBS containing 2% FCS and then incubated on ice in the presence of LGR5-Fc, LRP6-ECD-Fc (containing the extracellular domain of human LRP6 fused to an Fc domain), LRP6E1-2-Fc (containing amino acids 1-629 of human LRP6 fused to an Fc domain), or various FZD-Fc constructs, including FZD1-10. RSPO1 transfected cells interacted with LGR5 but did not interact with any FZD constructs (FIG. 7A). Only a weak interaction between RSPO1 and the WNT co-receptor LRP6 was detected.

Figure 7B:
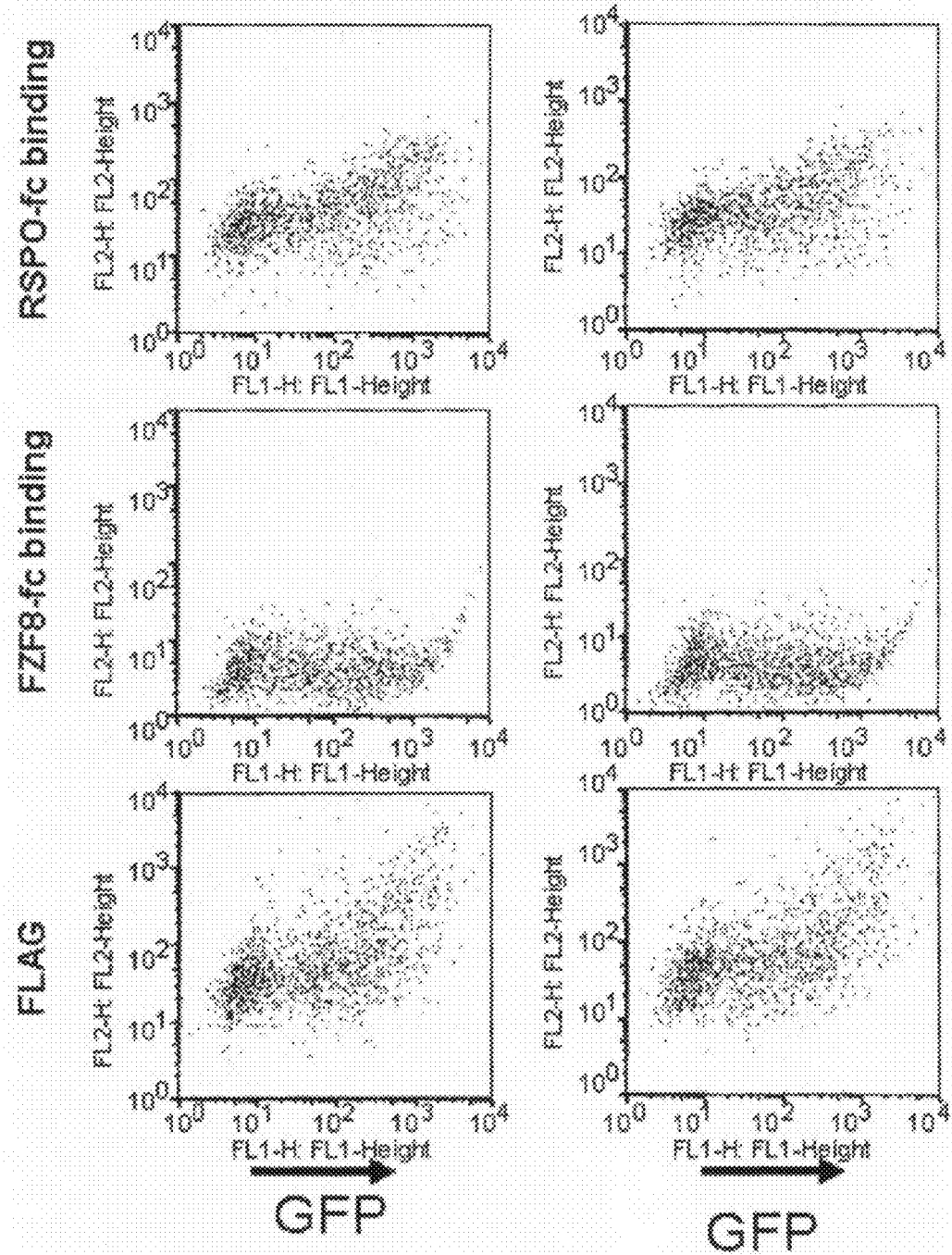

In certain embodiments, binding between soluble RSPO1 and cell-surface LGR5 was determined. A variant cell-surface LGR5 protein was generated by ligating amino acids 22-564 of LGR5 to an N-terminal FLAG tag and to the transmembrane domain of CD4 using standard recombinant DNA techniques (FLAG-LGR5-CD4TM). HEK 293 cells were transiently transfected with FLAG-LGR5-CD4TM and GFP. After 48 hours, cells were suspended in ice cold PBS containing 2% FCS and heparin and then incubated on ice in the presence of RSPO1-Fc, FZD8-Fc, or a FLAG antibody as a positive control. Soluble RSPO1 interacts with LGR5 transfected cells but soluble FZD8 did not (FIG. 7B).

To determine whether other RSPO family members also were able to bind to LGR5 additional studies were performed examining the interaction of each RSPO family member with LGR5. HEK 293 cells were transiently transfected with FLAG-LGR5-CD4TM and GFP. After 48 hours, cells were suspended in ice cold PBS containing 2% FCS heparin and then incubated on ice in the presence of RSPO1-Fc, RSPO2-Fc, RSPO3-Fc, RSPO4-Fc, FZD8-Fc, as indicated (FIG. 7C) or a FLAG antibody as a positive control. Each RSPO family member interacted with the LGR5 transfected cells.

Example 3

Generation of Anti-LGR5 Antibodies

Example 2 identifies an alternative pathway to beta-catenin activation via RSPO1 and LGR5. Blocking the interaction between RSPO and LGR proteins, therefore, could disrupt over-activation of beta-catenin signaling associated with tumorigenicity. In certain embodiments, antibodies against a LGR protein act as a cancer therapeutic by disrupting LGR signaling. In certain embodiments, antibodies against LGR5 disrupt the interaction between RSPO1 and LGR5.

This example describes the generation of antibodies against LGR5. Similar techniques are used to generate antibodies against LGR4 and LGR6.

Antigen Production

In certain embodiments, recombinant full-length or partial protein fragments of human LGR5 or an extracellular domain of human LGR5 are generated as antigens for antibody production. Standard recombinant DNA technology is used to isolate polynucleotides encoding LGR5. These polynucleotides are then ligated in-frame to protein tag sequence, including, for example, a human Fc, a histidine-tag, a FLAG-tag, or other suitable protein tag, and cloned into a transfer plasmid vector for baculovirus mediated expression in insect cells. Standard transfection, infection, and cell culture protocols are then used to produce recombinant insect cells expressing the corresponding LGR5 polypeptides (O'Reilley et al., Baculovirus expression vectors: A Laboratory Manual, Oxford: Oxford University Press (1994)). Antigen protein is purified from insect cell lysates using affinity chromatography. Purified antigen protein is dialyzed against PBS (pH=7), concentrated to approximately 1 mg/ml, and sterile filtered in preparation for immunization.

Immunization

Mice (n=3) are immunized with purified LGR5 antigen protein (Antibody Solutions; Mountain View, Calif.) using standard techniques. Blood from individual mice is screened approximately 70 days after initial immunization for antigen recognition using ELISA and FACS analysis. The two animals with the highest antibody titers are selected for final antigen boost after which spleen cells are isolated for hybridoma production. Hybridoma cells are plated at 1 cell per well in 96 well plates, and the supernatant from each well screened by ELISA and FACS analysis against antigen protein. Several hybridomas with high antibody titer are selected and scaled up in static flask culture. Antibodies are purified from the hybridoma supernatant using protein A or protein G agarose chromatography and antibodies are tested by FACS sorting of cells expressing LGR5.

FACS Analysis

To select monoclonal antibodies produced by hybridoma clones that recognize native cell-surface LGR5 protein, FACs analysis is used. In one example, to facilitate the screening of cells by FACS, an isotype control mouse IgG1κ antibody, and anti-LGR5 monoclonal antibodies are conjugated to Alexa Fluor™ 647 (AF647) using Invitrogen kit #A-20186. HEK 293 cells are transiently co-transfected with expression vectors encoding a cell-associated LGR5 construct and GFP. Twenty-four to 48-hours post-transfection cells are collected in suspension and incubated on ice with anti-LGR5 antibodies compared to control IgG1 antibodies to detect background antibody binding. The cells are washed and then sorted by FACS to identify antibody binding to surface expressed LGR5, respectively.

Figure 8:
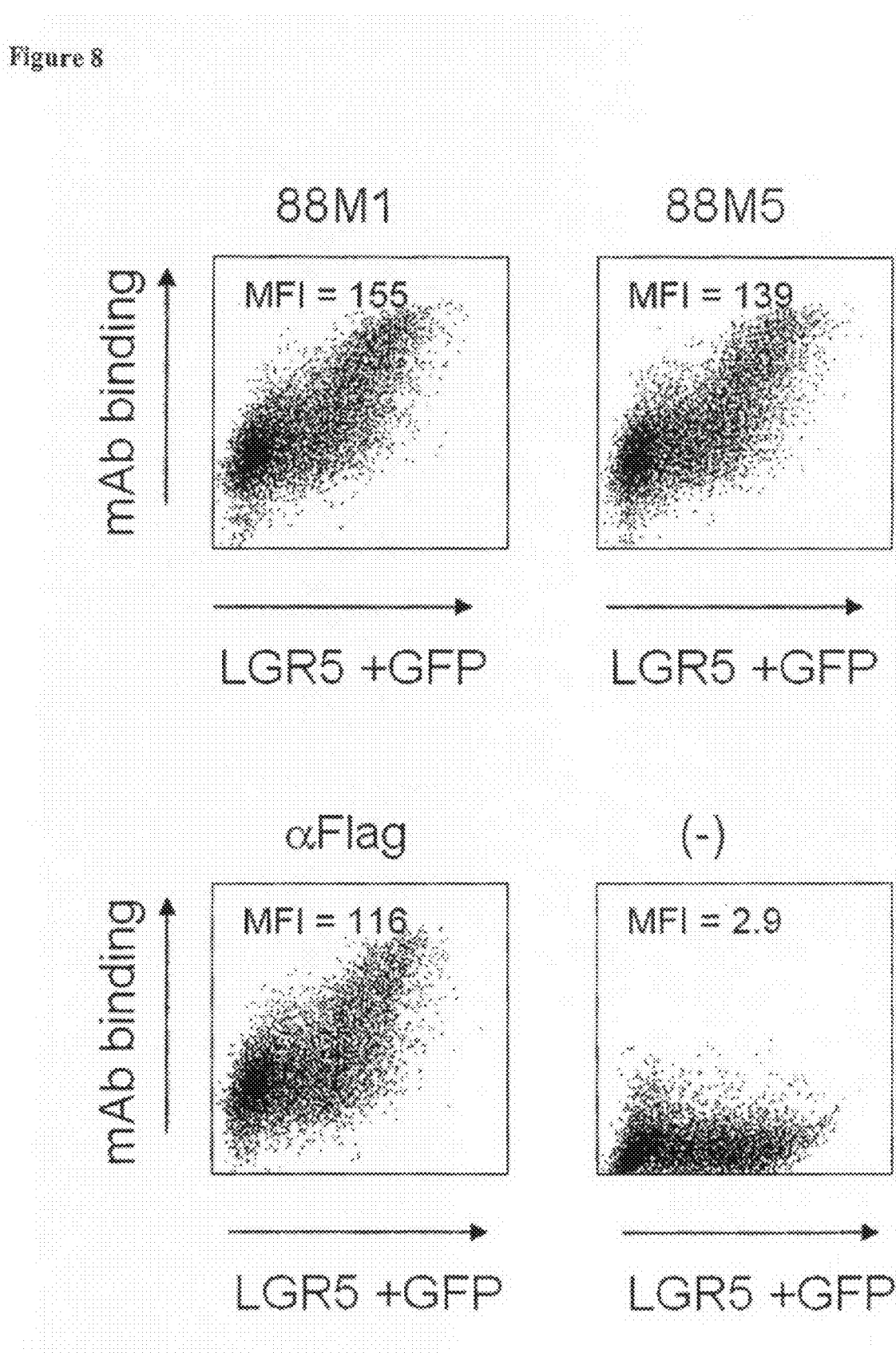
FIG. 8. Identification of mAbs to LGR5. HEK 293 cells transiently transfected with FLAG-LGR5-CD4TM and GFP were incubated with an irrelevant antibody as a negative (IgG1 control), or with anti-FLAG antibody as positive control for LGR5 expression, or a mAbs to LGR5 (88M1, 88M5), followed by incubation with PE-conjugated fluorescent anti-mAb secondary reagent. Samples were then analyzed by flow cytometry. 88M1 and 88M5 were found to display specific LGR5 binding.

In one experiment, monoclonal antibodies produced by hybridoma clones that recognize native cell-surface LGR5 protein were selected using FACs analysis. HEK 293 cells were transiently co-transfected with expression vectors encoding a cell-associated LGR5 construct (FLAG-LGR5-CD4TM) and GFP. Twenty-four to 48-hours post-transfection, the cells were collected in suspension and incubated on ice with an irrelevant antibody as a negative (IgG1 control), or with anti-FLAG antibody as positive control for LGR5 expression, or with a mAbs to LGR5 (88M1, 88M5), followed by incubation with PE-conjugated fluorescent anti-mAb secondary reagent. The cells were washed and then sorted by FACS to identify antibody binding to surface expressed LGR5, respectively. In this manner antibodies to LGR5 were identified (FIG. 8). The monoclonal antibodies 88M1 and 88M5 were found to display specific LGR5 binding. Further, one can use FACS analysis to select antibodies that disrupt the interaction between an RSPO protein and an LGR protein (e.g., LGR5). For example, one can measure the binding of an RSPO to LGR5 by flow cytometry in the presence or absence of an antibody to LGR5.

Figure 9:
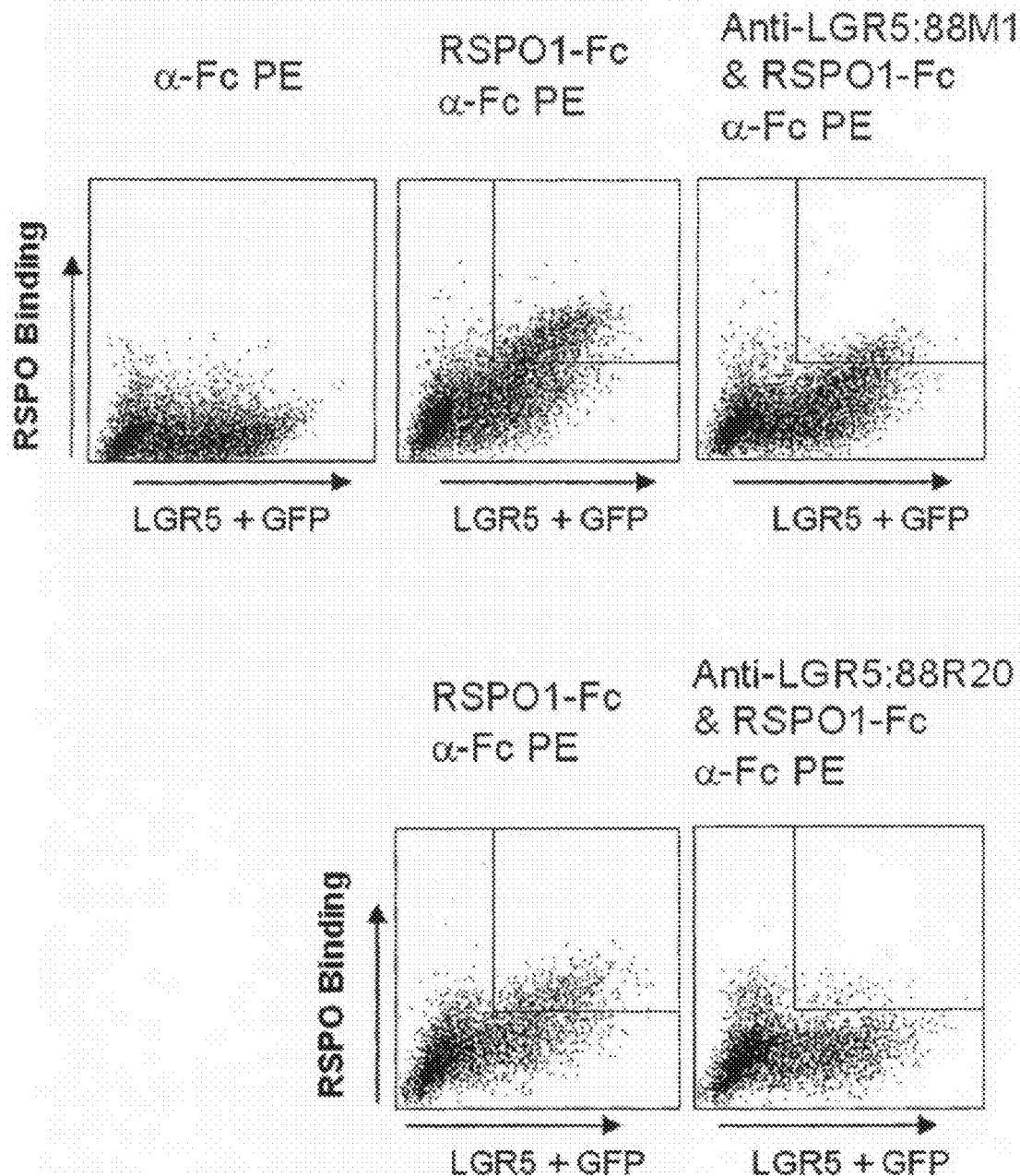
FIG. 9. Identification of mAb that inhibits RSPO binding to LGR5. HEK 293 cells transiently transfected with FLAG-LGR5-CD4TM and GFP. Binding of fusion protein RSPO1-fc to transfected cells was detected by incubation PE-conjugated anti-human-fc. The impact of anti-LGR5 antibodies 88M1 and 88R20 on RPSO binding was assessed by incubation of the cells with 88M1 as indicated and analysis with flow cytometry. The experiment shows that 88M1 and 88R20 reduced the RPSO1 binding to LGR5.

As shown (FIG. 9), the monoclonal antibody 88M1 and the antibody 88R20 were both identified as anti-LGR5 antibodies that inhibit the binding of RSPO to LGR5. HEK 293 cells were transiently transfected with FLAG-LGR5-CD4TM and GFP. Binding of fusion protein RSPO1-Fc to transfected cells was detected by incubation with PE-conjugated anti-human-Fc. The impact of anti-LGR5 antibody 88M1 and 88R20 on RSPO1-Fc binding was assessed by incubation of the transfected cells with 88M1 or 88R20 as indicated and analysis with flow cytometry. The experiment shows that 88M1 and 88R20 reduced the binding of RSPO1-Fc to LGR5 on the transfected cells Chimeric Antibodies After monoclonal antibodies that specifically recognize LGR5 are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human IgG1 heavy-chain and kappa light-chain constant region genes on the same plasmid (Preston et al., 1998, Infection & Immunity 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against LGR5 can require further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In alternative embodiments, human antibodies that specifically recognize an extracellular domain of LGR5 are isolated using phage display technology. A synthetic antibody library containing human antibody variable domains (MorphoSys, Munich, Germany) is screened for specific and high affinity recognition of an antigen described above. CDR cassettes in the library are specifically exchanged via unique flanking restriction sites for antibody optimization. Optimized human variable regions are then cloned into an Ig expression vector containing human IgG1 heavy-chain and kappa light-chain for expression of human antibodies in CHO cells.

A further description of exemplary methods for generating human antibodies to LGR5 is provided in Example 6, below.

Example 4

In Vivo Prevention of Tumor Growth by Targeting LGR5

This example described the use of biomolecules targeting LGR5 to effect the growth of tumor cells in vivo. In certain embodiments, antibodies against LGR5 are used to inhibit the growth of tumor cells in vivo. Similar techniques are used with biomolecules targeting LGR4 and LGR6.

Tumor cells from patient samples that have been passaged as a xenograft in mice are prepared for injection into experimental animals. Tumor tissue is removed under sterile conditions, cut up into small pieces, minced completely using sterile blades, and single cell suspensions obtained by enzymatic digestion and mechanical disruption. The resulting tumor pieces are mixed with ultra-pure collagenase III in culture medium (200-250 units of collagenase per mL) and incubated at 37° C. for 3-4 hours with pipetting up and down through a 10-mL pipette every 15-20 min. Digested cells are filtered through a 45 ul nylon mesh, washed with RPMI/20% FBS, and washed twice with HBSS. Dissociated tumor cells are then injected into NOD/SCID mice at 6-8 weeks to elicit tumor growth. In certain embodiments, breast tumor cells are injected at 50,000 cells in 100 ul into the right mammary fat pad (n=10) along with the implantation of an estrogen pellet. In certain embodiments, colon tumor cells are injected at 50,000 cells in 100 ul into the right flank region (n=10).

In alternative embodiments, dissociated tumor cells are first sorted into tumorigenic and non-tumorigenic cells based on cell surface markers before injection into experimental animals. Specifically, tumor cells dissociated as described above are washed twice with HBSS containing 2% heat-inactivated calf serum (HICS) and resuspended at $10^6$ cells per 100 ul. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin− tumorigenic cells are then injected subcutaneously into NOD/SCID mice to elicit tumor growth.

In certain embodiments, tumors are allowed to grow to approximately 75 mm² before treatment begins. In certain embodiments, treatment begins two days following cell injections. In certain embodiments, each injected animal receives 10 mg/kg of an anti-LGR5 antibody (e.g., 88M1) or a control antibody. Animals receive antibody treatment two times per week for a total of 6 to 8 weeks, and tumor size is assessed twice a week. Animals treated with anti-LGR5 antibodies are expected to show significantly reduced tumor cell growth compared to control injected animals.

Example 5

Treatment of Human Cancers by Disruption of LGR5 Signaling

This example describes methods for treating cancer in human patients using biomolecules that disrupt functional LGR5 signaling. In certain embodiments, antibodies against LGR5 are used to inhibit growth of a solid tumor comprising solid tumor stem cells. Similar techniques are used with biomolecules targeting LGR4 and LGR6.

In certain embodiments, the presence of cancer stem cell marker expression is first determined from a tumor biopsy. Tumor cells from a biopsy from a patient diagnosed with cancer are removed under sterile conditions. In certain embodiments, the tissue biopsy is fresh-frozen in liquid nitrogen, embedded in O.C.T., and cut on a cryostat as 10 um sections onto glass slides. In certain embodiments, the tissue biopsy is formalin-fixed, paraffin-embedded, and cut on a microtome as 10 um section onto glass slides. Sections are incubated with antibodies against a cancer stem cell marker such as LGR5 to detect protein expression. In certain embodiments, the presence of cancer stem cells is determined by FACS. Tissue biopsy samples are cut up into small pieces, minced completely using sterile blades, and cells subject to enzymatic digestion and mechanical disruption to obtain a single cell suspension. Dissociated tumor cells are then incubated with anti-ESA and -CD44 antibodies and the presence of tumor stem cells is determined by flow cytometry.

Cancer patients whose tumors are diagnosed as expressing a cancer stem cell marker are treated with a molecule that disrupts functional LGR5 signaling. In certain embodiments, the molecule comprises anti-LGR5 antibodies. Humanized or human monoclonal LGR5 antibodies generated as described above are purified and formulated with a suitable pharmaceutical carrier in PBS for injection. Patients are treated once a week for at least 10 weeks, but in certain cases once a week for at least about 14 weeks. Each administration should be a pharmaceutically effective dose about 2 to about 100 mg/ml and in certain cases between about 5 to about 40 mg/ml. Treatment can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Example 6

Human Antibodies Against LGR5

In certain embodiments, human antibodies that specifically recognize LGR5, were isolated using phage display. Generally, a synthetic antibody library containing human antibody variable domains is panned for specific and high affinity recognition of the extracellular domains of LGR5 receptor. Human variable regions are then cloned into an Ig expression vector containing human IgG$_2$ heavy-chain and light-chain (kappa or lambda) for expression of human antibodies in CHO cells.

In certain embodiments, phage display identified a specific Fab that binds to the RSPO1 ligand binding domain within LGR5. In certain embodiments, 2×10$^{13}$ Fab displaying phage particles from a human Fab phage library were incubated with cells expressing full length recombinant protein or passively immobilized recombinant protein fragments, non-specific phage were washed off, and then specific phage were eluted with either low pH (cells) or DTT (recombinant protein). The eluted output was used to infect TG1 F+ bacteria, rescued with helper phage, and then Fab display induced with IPTG (0.25 mM). The output of this rescued round one served as the starting point for further selection rounds. In all cases, selections were continued to round 3 and then the output was screened in ELISA for specific Fabs to each antigen.

The phage display library was panned for binding to the recombinant LGR5 extracellular domain Fc fusion. Fabs were surveyed for their ability to bind to LGR5 and block its interaction with RSPO1. 88R20 and 88R21Fabs specifically bound and blocked LGR5-RSPO1 binding in a FACS based assay. These Fabs were reformatted to full length IgG and their blocking ability was reconfirmed. The sequences of the 88R20 and 88R21 Fabs are provided below.

What is claimed is:

1. An isolated monoclonal antibody that specifically binds to an extracellular domain of a human leucine-rich repeat-containing G protein-coupled receptor (LGR) protein, wherein the antibody is a chimeric, humanized, or human antibody and wherein said antibody:
   (a) disrupts binding of a human R-spondin (RSPO) protein to the LGR protein; and/or
   (b) disrupts RSPO activation of LGR signaling.

2. The antibody of claim 1, wherein the human RSPO protein is selected from the group consisting of RSPO1, RSPO2, RSPO3, and RSPO4.

3. The antibody of claim 1, wherein the LGR protein is LGR5.

4. The antibody of claim 3, wherein the extracellular domain comprises amino acids 22-564 of human LGR5 (SEQ ID NO: 1).

5. The antibody of claim 1, wherein the LGR protein is LGR4 or LGR6.

6. A cell line producing the antibody of claim 1.

7. A hybridoma cell line having ATCC deposit number PTA-9342.

8. A monoclonal antibody 88M1 produced by the hybridoma cell line of claim 7.

9. An isolated antibody comprising the heavy chain CDRs and the light chain CDRs of the antibody of claim 8.

10. An isolated antibody that competes with the antibody of claim 8 in a competitive binding assay.

11. An isolated antibody that binds LGR5, comprising:
    (a) a heavy chain CDR1 comprising SSYAIS (SEQ ID NO:35), a heavy chain CDR2 comprising GIIPIFG-MANYAQKFQG (SEQ ID NO:36), and a heavy chain CDR3 comprising YDFITHFDF (SEQ ID NO:37);and
    (b) a light chain CDR1 comprising RASQSVSSNYLA (SEQ ID NO:32), a light chain CDR2 comprising DAS-NRAT (SEQ ID NO:33), and a light chain CDR3 comprising QQMDDFPM (SEQ ID NO:34).

12. An isolated antibody that binds LGR5, comprising:
    (a) a heavy chain CDR1 comprising SNYAIG (SEQ ID NO:41), a heavy chain CDR2 comprising GIRPNFG-WAKYAQKFQG (SEQ ID NO:42), and a heavy chain CDR3 comprising YGQGHFPSAFDY (SEQ ID NO:43); and
    (b) a light chain CDR1 comprising TGTNSDVG-TYNYVH (SEQ ID NO:38), a light chain CDR2 comprising DGSNRPSG (SEQ ID NO:39), and a light chain CDR3 comprising QAYDSHSFNI (SEQ ID NO:40).

13. An isolated antibody that binds LGR5, comprising:
    (a) a heavy chain variable region having at least 95% sequence identity to SEQ ID NO:45; and
    (b) a light chain variable region having at least 95% sequence identity to SEQ ID NO: 44.

14. An isolated antibody that binds LGR5, comprising:
    (a) a heavy chain variable region having at least 95% sequence identity to SEQ ID NO:47; and
    (b) a light chain variable region having at least 95% sequence identity to SEQ ID NO:46.

15. The antibody of claim 1, which inhibits growth of a solid tumor comprising solid tumor stem cells.

16. An isolated antibody that binds LGR5, comprising:
    (a) a heavy chain variable region comprising SEQ ID NO:45; and
    (b) a light chain variable region comprising SEQ ID NO: 44.

17. An isolated antibody that binds LGR5, comprising:
    (a) a heavy chain variable region comprising SEQ ID NO:47; and
    (b) a light chain variable region comprising SEQ ID NO:46.

* * * * *